US008927698B2

(12) United States Patent
Dékany et al.

(10) Patent No.: US 8,927,698 B2
(45) Date of Patent: *Jan. 6, 2015

(54) METHOD FOR THE SYNTHESIS OF A TRISACCHARIDE

(75) Inventors: Gyula Dékany, Queensland (AU);
Istvan Bajza, Debrecen (HU); Julien Boutet, La Plaine sur Mer (FR); Ignacio Pérez Figueroa, Miami, FL (US);
Markus Hederos, Svedala (SE); Ferenc Horvath, Pilisszentkereszt (HU);
Piroska Kovács-Pénzes, Jászberény (HU); Lars Kröger, Hamburg (DE);
Johan Olsson, Stockholm (SE);
Christoph Röhrig, Mühlingen (DE);
Andreas Schroven, Barssel (DE);
Ioannis Vrasidas, Thessaloniki (GR)

(73) Assignee: Glycom A/S, Lyngby (DK)

(*) Notice: Subject to any disclaimer, the term of this patent is extended or adjusted under 35 U.S.C. 154(b) by 544 days.

This patent is subject to a terminal disclaimer.

(21) Appl. No.: 13/263,716

(22) PCT Filed: Apr. 7, 2010

(86) PCT No.: PCT/EP2010/054608
§ 371 (c)(1),
(2), (4) Date: Dec. 30, 2011

(87) PCT Pub. No.: WO2010/115935
PCT Pub. Date: Oct. 14, 2010

(65) Prior Publication Data
US 2012/0116065 A1     May 10, 2012

(30) Foreign Application Priority Data

Apr. 7, 2009   (DK) .................... 2009 00469

(51) Int. Cl.
| *C07H 3/06* | (2006.01) |
| *C07H 15/203* | (2006.01) |
| *C07H 15/26* | (2006.01) |
| *C07H 1/00* | (2006.01) |
| *C07H 15/04* | (2006.01) |

(52) U.S. Cl.
CPC ............... *C07H 3/06* (2013.01); *C07H 15/04* (2013.01); *C07H 15/203* (2013.01); *C07H 1/00* (2013.01)
USPC ........... 536/18.6; 536/4.1; 536/116; 536/120; 536/123.1

(58) Field of Classification Search
CPC .......... C07H 3/06; C07H 1/00; C07H 15/203; C07H 15/04
USPC ................ 536/18.6, 116, 120, 123.1, 4.1
See application file for complete search history.

(56) References Cited

U.S. PATENT DOCUMENTS 5,438,124 A     8/1995   Matta et al.

OTHER PUBLICATIONS

Pohl et al, Tetrahedron Letters, 1997, 38(40), 6985-6988.*
Abbas S A et al, "Synthesis of 0-alpha-l-fucopyranosyl-(1->)-0-beta-d-galactophranosyl (1->4)-d-glucopyranose (2'-0-alpha-l-fucopyranosyl-lactose)", Carbohydrate Research, Jan. 15, 1981, vol. 88, No. 1, pp. 51-60, XP026743786, ISSN: 0008-6215, United Kingdom.
Fernandez-Mayoralas A et al, "Synthesis of 3- and 2'-fucosyl-lactose and 3,2'-difucosyl-lactose derivatives", Carbohydrate Research, Oct. 15, 1986, vol. 154, No. 1, pp. 93-101, XP026618813, ISSN: 008-6215(00)90025-9, United Kingdom.
Jain R K et al, "A convenient sythesis of O-$_x$-L-fucopyranosyl-(1→2)-O-β-D-glucopyranose (2'-O-$_x$-L-fucopyranosyl-lactose)",Carbohydrate Research, Jan. 3, 1991, vol. 212, pp. c1-c3.
Bornaghi L et al, "Methyl 3,4-O-dibenzoyl-2-O-benzyl-1-thio-β-L-fucopyranoside", Acta Crystallographica Section E, Aug. 5, 2005, vol. 61, pp. 02899-02901, XP009137746, DOI: 10.1107/S160053680502516X, Great Britain.
Kiyoi T et al, A Highly Practical Synthesis of the Sialyl Lexis X Pentasaccharide an Investigation of Binding to E-, P-, and L-Selectins, Bioorganic & Medicinal Chemistry, Feb. 26, 1996, vol. 4, No. 8, pp. 1167-1176, 0968-0896/96, Great Britain.
Zeigler T, "Synthesis of the 5-aminopentyl glycoside ofβ-D-Gal p-(1→4) β-D-GlcpNAc(1→3)-L-Fucp and fragments thereof related to glycopeptides of human Chritmas factor and the marine sponge Microciona prolifera", Carbohydrate Research, Mar. 25, 1994, vol. 262, pp. 195-212, XP-002597319, SSDI 008-6215.
Kakali S et al, Synthesis of Tetrasaccharide Repeating Unit of the O-Antigen from Enterohemorrhagic, *Escherichia coli* 0157 in the form of its 2-(trimethylsilyl)ethyl Glycoside, Journal of Carbohydrate Chemistry, Aug. 12, 2005, vol. 25, pp. 53-68, XP009137748, ISSN: 0732-8303, 1532-2337, DOI:10.1080/07328300500495878, India.

(Continued)

*Primary Examiner* — Ganapathy Krishnan
(74) *Attorney, Agent, or Firm* — McHale & Slavin, P.A.

(57) ABSTRACT

The present invention relates to an improved synthesis of a trisaccharide of the formula, novel intermediates used in the synthesis and the preparation of the intermediates.

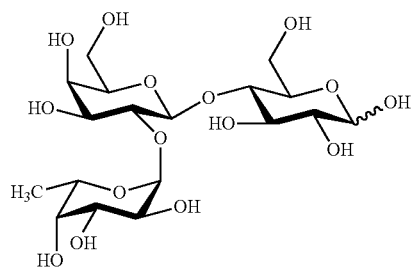

19 Claims, No Drawings

(56) References Cited

OTHER PUBLICATIONS

Izumi M et al, "Synthesis of 5-Thio-L-fucose-Containing Disaccharides, as Sequence-Specific Inhibitors, and 2'-Fucosyllactose, as a Substrate of α-L-Fucosidases", J Org. Chem., 1997, vol. 62, No. 4, pp. 992-998, Japan.

Rencurosi, A et al, "Improvement on Lipase Catalysed Regioselective O-Acylation of Lactose: A Convenient Route to 2'-O-Fucosyllactose", J. Carbohydrate Chemistry, Sep. 5, 2001, vol. 20 No. 7-8, pp. 761-765, Novara, Italy.

* cited by examiner

METHOD FOR THE SYNTHESIS OF A TRISACCHARIDE

CROSS-REFERENCE TO RELATED APPLICATIONS

This application is a §371 national stage entry of International Application No. PCT/EP2010/054608, filed Apr. 7, 2010, which claims priority to Denmark Patent Application No. PA 2009 00469, filed Apr. 7, 2009, the entire contents of which are incorporated herein by reference.

FIELD OF THE INVENTION

The present invention relates to a novel synthesis of a trisaccharide, novel intermediates used in the synthesis and the preparation of the intermediates.

BACKGROUND OF THE INVENTION

In the present years commercialization efforts for the synthesis of complex carbohydrates including secreted oligosaccharides have increased significantly due to their roles in numerous biological processes occurring in living organisms. Secreted oligosaccharides such as human milk oligosaccharides (HMOs) are becoming important commercial targets for nutrition and therapeutic industries. However, the syntheses and purification of these oligosaccharides and their intermediates remained a challenging task for science. One of the most important human milk oligosaccharides is 2'-O-fucosyllactose (α-L-fucopyranosyl-(1→2)-β-D-galactopyranosyl-(1→4)-D-glucose, "2'-FL") found in the highest concentration in mother's milk.

Scheme 1. The structure of 2'-O-fucosyllactose

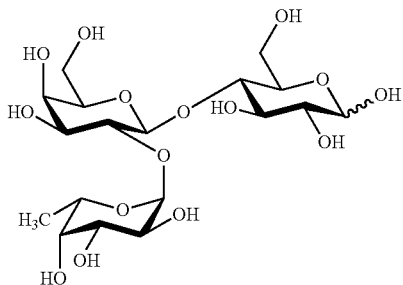

Several biological roles of 2'-O-fucosyllactose have been suggested including but not limited to its prebiotic, antibacterial, antiviral, immune system enhancing, brain development enhancing, etc. effects making it an attractive target for large scale production/isolation/purification for nutritional and therapeutic industries. 2'-O-fucosyllactose has been synthesised by both chemical and enzymatic methodologies but commercially attractive production processes have not been developed due to lack of efficient purification and synthetic approaches. According to present scientific knowledge 2'-O-fucosyllactose is not a crystalline trisaccharide making the development of large scale/low cost manufacturing technologies suitable for the manufacture of high purity 2'-O-fucosyllactose a challenging task.

It is possible to obtain 2'-O-fucosyllactose by four different approaches using isolation, chemical synthesis, enzymatic synthesis and biotechnological methodologies.

The first mentioning of HMOs in the literature appeared in the 1950's. At these times specific human milk oligosaccharides were isolated from human milk by using sophisticated chromatographic protocols. However, the purities of such early isolated samples are rather uncertain due to the high number of human milk oligosaccharide isomers present in mother's milk. For example, 2'-O-fucosyllactose and 3-O-fucosyllactose are both present in human milk and their chromatographic separation have been solved decades later. It has later been found that milk from other mammals also contain some of these oligosaccharides but in extremely low concentrations and ratios different from human milk. In the later years enormous progresses have been made in the production of 2'-O-fucosyllactose via chemical, enzymatic and biotechnological methodologies. However, most of these methodologies have not succeeded in large scale productions providing bulk quantities of 2'-O-fucosyllactose in a commercially attractive price range.

Enzymatic synthesis of 2'-O-fucosyllactose has developed significantly in the last decade by using enzyme cloning/mutating technologies. One specific approach has transferred a fucosidase enzyme into a 1,2-α-L-fucosynthase facilitating the synthesis of glycosidic linkages and avoiding hydrolysis of these at the same time. Unfortunately, 1,2-α-L-fucosynthases are not commercially available in large quantities and therefore to date are not suitable for manufacturing technology developments. A second enzymatic approach has been using α-(1→2)fucosyltransferase, α-(1→2)-L-galactosyltransferase for the creation of interglycosidic linkages. These enzymes are rather sensitive and not really suitable for large scale preparations. Additionally, such enzymes require sugar nucleotide type donors which are hardly available and are extremely expensive. A third enzymatic approach is based upon the use of retaining α-L-fucosidases but the achieved selectivities and yields are usually rather modest.

Either genetically engineered microorganisms or mammals are used in biotechnological methodologies for the synthesis of 2'-O-fucosyllactose. Such technologies use complex enzymatic systems facilitating both the biosynthesis of precursors and the required glycosylations. To date, such approaches face severe regulatory approval hurdles due to the use of genetically engineered organisms and potential contaminations of non-natural oligosaccharides.

Chemical syntheses have until now still been the most economically efficient way to produce 2'-O-fucosyllactose. The hurdles of large scale chemical synthesis are i.e. low stereoselectivities, low overall yields, use of sophisticated and expensive purification methodologies such as column chromatography, and the use of toxic reagents not suitable for food/therapeutic product developments.

In prior art, all syntheses have been using a lactose acceptor and a fully protected L-fucose donor as essential building blocks. The differences among approaches are related to different protecting group strategies, glycosylation methodologies and final purification policies. According to our best knowledge, the first chemical synthesis of 2'-O-fucosyllactose was published in 1981 [1] and since then four further chemical [2-5] and one chemoenzymatic [6] syntheses have been published.

The first chemical synthesis of 2'-O-fucosyllactose was published by K. L. Matta and co-workers in 1981 [1] using a 6-O-benzoylated lactose acceptor and a tri-O-benzylated α-fucopyranosyl bromide donor followed by successive removal of the protecting groups. The synthesis comprises several chromatographic purification steps in the intermediate stages in order to reach a final intermediate which contains only benzyl protective groups. This compound was chromatographed and the purified sample was crystallized from methanol-ether as a dihydrate. However, this dihydrate proved to be rather inconvenient for the last deprotection (catalytic hydrogenolysis) step due to its awkward solubility. In fact, extremely diluted solutions can only be made from such a dihydrate in mixtures of alcohols/water/acetic acid making it hardly suitable for the development of an efficient production technology. Furthermore, lack of crystalline intermediates all along the synthesis—both at disaccharide and trisaccharide stages—prevent the development of manufacturing technologies. Multiple chromatographic separations and the use of extremely sensitive per-O-benzylated bromosugar make the approach rather unsuitable for technology developments.

In 1986 M. Martin-Lomas [2] and co-workers published the synthesis of 2'-O-fucosyllactose preparing an isopropylidene-protected final 2'-FL intermediate. The final deprotection step is the cyclic ketal hydrolysis using 20% aqueous acetic acid. The synthetic strategy is utilizing a very rare lactose diol acceptor, which is difficult to make in large quantities. Actually, the precursor itself makes the approach uncompetitive for large scale technology developments. Furthermore, numerous chromatographic purifications are needed for intermediate isolations and the approach doesn't provide crystalline intermediates which might facilitate cheap purification options via crystallization. The final deprotection is a cyclic ketal hydrolysis which is a delicate step due to acid lability of the L-fucose residue. The hydrolytic cleavage condition of the cyclic ketal has to be rather gentle to prevent by-product formations. However, gentle hydrolysis condition ends up with the presence of unhydrolyzed cyclic ketals in the reaction mixture. Thus, the crude 2'-O-fucosyllactose product requires further chromatographic purifications. Due to the disadvantages listed above the approach is not suitable for manufacturing technology developments.

K. L. Matta and co-workers published additional two syntheses [3, 4] choosing a protection group strategy which facilitated a trifluoroacetic acid assisted hydrolysis of the final 2'-FL intermediate. Both syntheses use the same acceptor but different 4-methoxybenzylated donor molecules. One approach uses n-pentenyl glycoside activated by IDCP while the second approach is based upon thioglycoside activation. The use of pentenyl glycoside with IDCP promoter prevents itself the development of production technologies due to the limited availability of the donor and the high price of the activator. In the case of thioglycoside activation, the fucosylation step provided an α/β-mixture in the ratio (9:1) and a rather difficult chromatographic purification was needed to separate the desired stereoisomer from the unwanted β-product. Thus, none of these methodologies have potentials for multi-ton-scale production of 2'-O-fucosyllactose.

In 1997 H. Hashimoto and co-workers developed a synthesis strategy using acid/oxidation labile protecting groups on both acceptor and donor molecules (isopropylidene and 4-methoxybenzyl) which were removed in trisaccharide intermediate via ceric ammonium nitrate treatment [5]. The approach provides polar products which are rather difficult to handle and contaminated by large quantity of ceric ammonium salts. Both the 2'-O-fucosyllactose and the inorganic impurity were water soluble substances, thus, O-acetylation followed by Zemplén deprotection was needed as the essential purification step of the synthesis. The approach has numerous drawbacks such as use of IDCP as a coupling reagent, removal of p-methoxybenzyl groups using CAN (expensive and toxic) and O-deacetylation of the final 2'-FL intermediate using sodium methoxide in the presence of base sensitive end-product. In general, high purity of 2'-O-fucosyllactose cannot be produced when reducing sugars are treated with strong bases.

In year 2001 L. Lay and co-workers introduced a synthesis of 2'-O-fucosyllactose using both enzymatic and chemical procedures [6]. In this approach a β-benzyllactoside derived acceptor was synthesized using enzymatic manipulations for installing orthogonal protecting groups in a regioselective manner. The last part of the synthetic strategy consists of three steps, the fucosylation, an O-deacetylation and a hydrogenolysis. Unfortunately, the method has never generated commercialization interest due to the relatively modest yields of lipase assisted acylation, the use of toxic and explosive hydrazine derivatives and lack of crystalline intermediates. Multiple chromatographic steps all along the synthesis prevented the development of manufacturing technologies.

In summary, isolation technologies have never been able to provide large quantities of human milk oligosaccharides including 2'-O-fucosyllactose due to the large number of oligosaccharides present in human milk. Additionally, the presence of regioisomers characterized by extremely similar structures further made separation technologies unsuccessful. Enzymatic methodologies suffer from the low availability of enzymes, extremely high sugar nucleotide donor prices and regulatory difficulties due to the use of enzymes produced in genetically modified organisms. The preparation of human milk oligosaccharides via biotechnology has huge regulatory obstacles due to the potential formation of several unnatural glycosylation products. To date, all the chemical methods developed for the synthesis of 2'-O-fucosyllactose have several drawbacks which prevented the preparation of even multigram quantities of 2'-O-fucosyllactose. The most severe drawback of chemical approaches is the lack of design for crystalline intermediates to facilitate low cost purification methodologies and to enhance scale-up opportunities. Thus, the demand for the development of a robust synthetic approach suitable for the production of 2'-O-fucosyllactose has been increasing.

The present invention provides methodology suitable for large scale manufacturing of 2'-O-fucosyllactose and novel intermediates for the synthesis of 2'-O-fucosyllactose. The invention is based upon the utilisation of hydrogenolysis of O-benzyl/substituted O-benzyl moieties of novel protected 2'-O-fucosyllactose intermediates. Additionally, it is also an important characteristic of the present invention that the above-mentioned novel O-benzylated/substituted O-benzylated 2'-O-fucosyllactose intermediates have nice crystalline properties assisting powerful purification processes. For example, the realisation of highly crystalline properties of 2'-O-fucosyllactose derivatives allowed the development of powerful manufacturing procedures using entirely crystallisations for product/intermediate purifications. More importantly, the introduction of novel 2'-O-fucosyllactose intermediates provided by the present invention opens the very first opportunities for scale-up options. Before the present invention, complex reaction sequences had to be performed in a continuous manner due to lack of cheap purification options. The novel crystalline 2'-O-fucosyllactose intermediates allow the separation of chemical steps from each other providing real opportunities for scale-up developments. Thus, the crystalline novel intermediates provided by the present invention are responsible for the development of the very first 2'-O-fucosyllactose manufacturing technology suitable to give bulk quantities of high purity 2'-O-fucosyllactose for nutritional and pharmaceutical industries.

SUMMARY OF THE INVENTION

The first aspect of the present invention relates to the use of compounds of general formula 1 for the preparation of 2'-O-fucosyllactose, characterized in that a compound of general formula 1

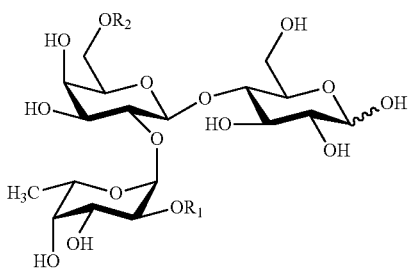

wherein $R_1$ is a group removable by hydrogenolysis and $R_2$ is a group removable by hydrogenolysis or H—or a hydrate or solvate thereof is subjected to catalytic hydrogenolysis.

The second aspect of the present invention provides novel compounds of general formula 1. Compounds of general formula 1 are converted to 2'-O-fucosyllactose by catalytic hydrogenolysis.

The third aspect of the present invention relates to a method for the preparation of compounds of general formula 1, characterized in that a compound of general formula 2

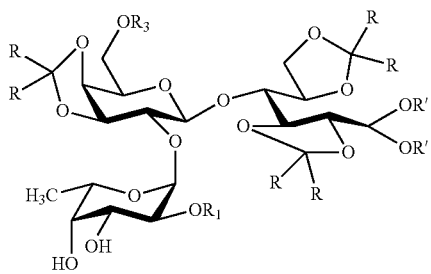

wherein $R_1$ is a group removable by hydrogenolysis, $R_3$ is a group removable by hydrogenolysis, acetal type group, silyl group or H, R is alkyl or two geminal R-groups with the carbon atom to which they are attached form a $C_3$-$C_6$ cycloalkyl ring, R' is alkyl—or hydrate or solvate thereof is subjected to acid catalyzed mild hydrolysis.

The fourth aspect of the present invention provides novel compounds of general formula 2.

The fifth aspect of the present invention is related to a method for the preparation of compounds of general formula 1, characterized in that a compound of general formula 3

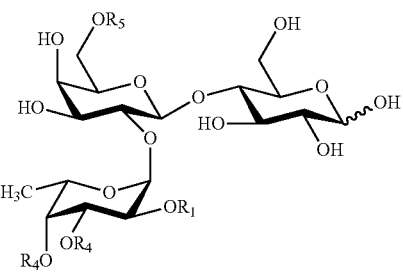

wherein $R_1$ is a group removable by hydrogenolysis, $R_4$ is optionally substituted acyl, $R_5$ is a group removable by hydrogenolysis or optionally substituted acyl—or a hydrate or solvate thereof is subjected to deacylation.

The sixth aspect of the present invention provides novel compounds of general formula 3.

The seventh aspect of the present invention relates to a method for the preparation of compounds of general formula 2, characterized in that a compound of general formula 4

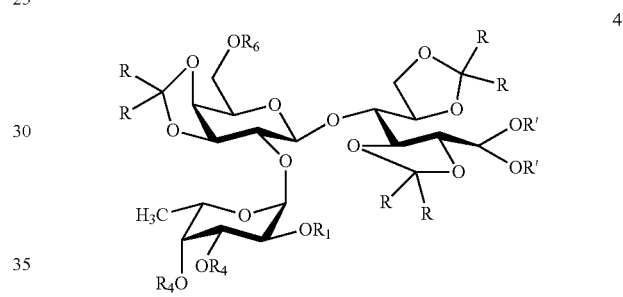

wherein $R_1$ is a group removable by hydrogenolysis, $R_4$ is optionally substituted acyl, $R_6$ is a group removable by hydrogenolysis, acetal type group, silyl group or optionally substituted acyl, R is alkyl or two geminal R-groups with the carbon atom to which they are attached form a $C_3$-$C_6$ cycloalkyl, R' is alkyl—or a hydrate or solvate thereof is deacylated.

The eighth aspect of the present invention relates to a method for the preparation of compounds of general formula 3, characterized in that a compound of general formula 4

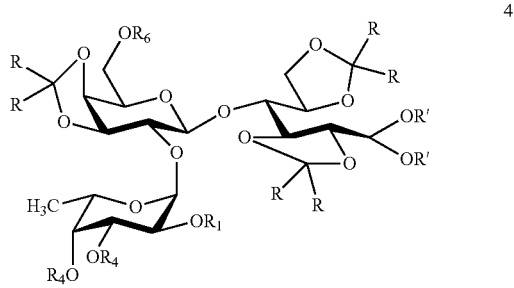

wherein $R_1$ is a group removable by hydrogenolysis, $R_4$ is optionally substituted acyl, $R_6$ is a group removable by hydrogenolysis, acetal type group, silyl group or optionally substituted acyl, R is alkyl or two geminal R-groups with the carbon atom to which they are attached form a $C_3$-$C_6$ cycloalkyl, R' is alkyl—or a hydrate or solvate thereof is subjected to acid catalyzed mild hydrolysis.

The ninth aspect of the present invention provides compounds of general formula 4.

The tenth aspect of the present invention is related to a method for the synthesis of a compound of general formula 4, characterized in that a compound of general formula 5

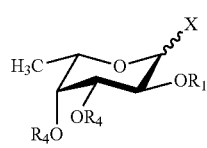

5 wherein $R_1$ and $R_4$ are defined above and X is halogen, —OC(=NH)CCl$_3$, —O-pentenyl, —OAc, —OBz or —SR$_7$, in which R$_7$ is alkyl or optionally substituted phenyl—is reacted with a compound of general formula 6

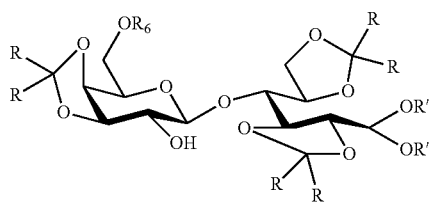

6 wherein R, R' and $R_6$ are defined above—under glycosylation condition.

The eleventh aspect of the present invention provides novel compounds of general formula 7

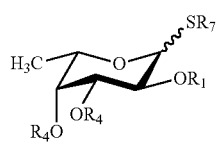

7 wherein $R_1$ is a group removable by hydrogenolysis, $R_4$ is optionally substituted acyl and $R_7$ is alkyl or optionally substituted phenyl, with the proviso that phenyl 3,4-di-O-acetyl-2-O-benzyl-1-thio-L-fucopyranoside, methyl 3,4-di-O-acetyl-2-O-benzyl-1-thio-L-fucopyranoside, ethyl 3,4-di-O-acetyl-2-O-benzyl-1-thio-L-fucopyranoside and ethyl 3,4-di-O-acetyl-2-O-(4-methoxybenzyl)-1-thio-L-fucopyranoside are excluded.

The twelfth aspect of the present invention provides a methodology suitable for the preparation of novel compounds of general formula 7, characterized in that a compound of general formula 8

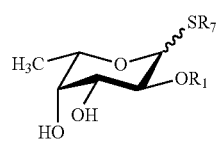

8 wherein $R_1$ and $R_7$ are defined above—is acylated by means of an acylating agent.

The thirteenth aspect of the present invention relates to a method for the preparation of 2'-O-fucosyllactose, characterized in that a compound of general formula 1

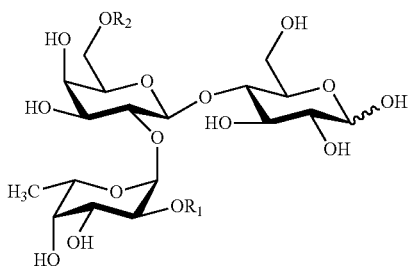

1 wherein $R_1$ is a group removable by hydrogenolysis and $R_2$ is a group removable by hydrogenolysis or H—or a hydrate or solvate thereof is subjected to catalytic hydrogenolysis.

DETAILED DISCLOSURE OF THE INVENTION

Throughout the present description, the term "alkyl" means a linear or branched chain saturated hydrocarbon group with 1-20 carbon atoms, preferably with 1-6 carbon atoms, like methyl, ethyl, n-propyl, i-propyl, n-butyl, i-butyl, s-butyl, t-butyl, n-hexyl, etc. The term "optionally substituted alkyl" intends to mean that the alkyl chain may either carry 1, 2, 3, 4 or 5 substituents or may be unsubstituted. The possible substituents, independently from each other, are selected from halogen, hydroxyl, optionally substituted alkyloxy, nitro, amino, optionally substituted alkylamino, optionally substituted dialkylamino, optionally substituted acyl, optionally substituted acylamino, carboxyl, optionally substituted alkyloxycarbonyl, carbamoyl, optionally substituted N-alkylcarbamoyl, optionally substituted N,N-dialkylcarbamoyl, optionally substituted N-arylcarbamoyl, thiol, optionally substituted alkylsulfanyl, optionally substituted aryl, optionally substituted aryloxy and optionally substituted aryloxycarbonyl. It is emphasized that the benzyl group is regarded as a member of substituted alkyls (i.e. phenylmethyl). Optionally substituted benzyl intends to mean optionally substituted phenyl (vide infra) attached to the methyl group, such as 4-methylbenzyl, 3-phenylbenzyl, 4-methoxybenzyl, etc.

In the present application, the term "aryl", either alone or when attached to another atom or group, refers to a homoaromatic group such as phenyl or naphthyl. If these groupings are "optionally substituted", they may either be unsubstituted or may bear 1, 2, 3, 4 or 5 groups including—independently from each other—optionally substituted alkyl, optionally substituted alkyloxy, halogen, nitro, amino, optionally substituted alkylamino, optionally substituted dialkylamino, optionally substituted acyl, optionally substituted acylamino, carboxyl, optionally substituted alkoxycarbonyl, carbamoyl, optionally substituted N-alkylcarbamoyl, optionally substituted N,N-dialkylcarbamoyl, thiol, optionally substituted alkylsulfanyl and optionally substituted phenyl.

In the present description, the term "acyl" represent an R"—C(=O)-group, wherein R" may be H, alkyl (see above) or aryl (see above), like formyl, acetyl, propionyl, butyryl, pivaloyl, benzoyl, etc. In case of "optionally substituted acyl", the alkyl or aryl residue may either be unsubstituted or may be substituted (vide supra) giving rise to acyl groups such as chloroacetyl, trichloroacetyl, 4-chlorobenzoyl, 4-nitrobenzoyl, 4-phenylbenzoyl, 4-benzamidobenzoyl, 4-(phenylcarbamoyl)-benzoyl, etc. If R means H or alkyl, the group is also named alkanoyl, and if R is aryl, the group is named aroyl.

The term "alkyloxy" or "alkoxy" means an alkyl group (see above) attached to the parent molecular moiety through an oxygen atom, such as methoxy, ethoxy, t-butoxy, etc. "Optionally substituted alkyloxy" or "optionally substituted alkoxy" refers to an alkyloxy group that may either be unsubstituted or may be substituted on the alkyl portion as defined above, such as trifluoromethoxy, 2,2,2-trichloroethoxy, etc.

"$C_3$-$C_6$ cycloalkyl" means cyclopropyl, cyclobutyl, cyclopentyl or cyclohexyl.

"$C_1$-$C_6$ alcohol" refers to hydroxy- or dihydroxy-alkanes having 1 to 6 carbon atoms such as methanol, ethanol, n-propanol, i-propanol, n-butanol, i-butanol, s-butanol, t-butanol, amylalcohol, n-hexanol, ethylene glycol, propylene glycol, etc.

"Halogen" means fluoro, chloro, bromo or iodo.

"Amino" refers to a —$NH_2$ group.

"Alkylamino" means an alkyl group (see above) attached to the parent molecular moiety through an —NH-group, such as methylamino, ethylamino, etc. "Optionally substituted alkylamino" refers to an alkylamino group that may either be unsubstituted or may be substituted on the alkyl portion as defined above.

"Dialkylamino" means two alkyl groups (see above), either identical or different ones, attached to the parent molecular moiety through a nitrogen atom, such as dimethylamino, diethylamino, etc. "Optionally substituted dialkylamino" refers to an dialkylamino group wherein at least one of the alkyl portions may either be unsubstituted or may be substituted as defined above.

"Acylamino" refers to an acyl group (see above) attached to the parent molecular moiety through an —NH-group, such as acetylamino (acetamido), benzoylamino (benzamido), etc. "Optionally substituted acylamino" is an acylamino group that may either be unsubstituted or may be substituted on the acyl portion as defined above.

"Carboxyl" denotes an —COOH group.

"Alkyloxycarbonyl" means an alkyloxy group (see above) attached to the parent molecular moiety through a —C(=O)-group, such as methoxycarbonyl, t-butoxycarbonyl, etc. "Optionally substituted alkyloxycarbonyl" is an alkyloxycarbonyl group that may either be unsubstituted or may be substituted on the alkyl portion as defined above, such as benzyloxycarbonyl, etc.

"Carbamoyl" is an $H_2N$—C(=O)-group.

"N-Alkylcarbamoyl" means an alkyl group (see above) attached to the parent molecular moiety through a —HN—C(=O)-group, such as N-methylcarbamoyl, etc. "Optionally substituted N-alkylcarbamoyl" is an N-alkylcarbamoyl group that may either be unsubstituted or may be substituted on the alkyl portion as defined above.

"N,N-Dialkylcarbamoyl" means two alkyl groups (see above), either identical or different ones, attached to the parent molecular moiety through a >N—C(=O)-group, such as N,N-methylcarbamoyl, etc. "Optionally substituted N,N-dialkylcarbamoyl" is a N,N-dialkylcarbamoyl group wherein at least one of the alkyl portions may either be unsubstituted or may be substituted as defined above.

"N-Arylcarbamoyl" is an aryl group (see above) attached to the parent molecular moiety through a —HN—C(=O)-group, such as N-phenylcarbamoyl, etc. "Optionally substituted N-arylcarbamoyl" is an N-arylcarbamoyl group that may either be unsubstituted or may be substituted on the aryl portion as defined above.

"Thiol" denotes a —SH group.

"Alkylsulfanyl" or "alkylthio" intends to mean an alkyl group (see above) attached to the parent molecular moiety through a sulphur atom, such as methylsulphanyl (methylthio), ethylsulphanyl (ethylthio), etc. "Optionally substituted alkylsulphanyl" refers to an alkylsulphanyl group that may either be unsubstituted or may be substituted on the alkyl portion as defined above.

"Aryloxy" means an aryl group (see above) attached to the parent molecular moiety through an oxygen atom, such as phenoxy, naphthyloxy, etc. "Optionally substituted aryloxy" refers to an aryloxy group that may either be unsubstituted or may be substituted on the aryl portion as defined above, such as 4-methoxy-phenoxy, 4-methylphenoxy, etc.

"Aryloxycarbonyl" means an aryloxy group (see above) attached to the parent molecular moiety through a —C(=O)-group, such as phenoxycarbonyl, etc. "Optionally substituted aryloxycarbonyl" is an aryloxycarbonyl group that may either be unsubstituted or may be substituted on the aryl portion as defined above.

"Azido" means a —$N_3$ group.

The synthesis of complex oligosaccharides such as 2'-O-fucosyllactose follows multistep synthetic pathways utilising protection and deprotection strategies. In spite of the diverse intermediate structures of oligosaccharide syntheses, the final synthetic targets are usually the unprotected oligosaccharides themselves featuring exclusive water solubility. Organic solvents commonly used in synthetic manufacturing processes are not suitable for the reactions of the very final stages of the oligosaccharide synthesis. Hydrogenolysis represents an exception among protecting group chemistries, in which water can be used as a solvent. Hydrogenolysis itself is a powerful deprotection process suitable to remove O-benzyl/substituted O-benzyl moieties from an oligosaccharide scaffold in almost a quantitative manner under extremely gentle conditions preventing by-product formations. It is also an advantage of hydrogenolysis as a final deblocking procedure within a complex synthetic pathway that only catalytic amount of reagents are required for the completion of the reaction providing exclusively toluene or substituted toluene derivatives as by-products. Both toluene and substituted toluene derivatives can easily be removed even in multi ton scales from water soluble oligosaccharide products via evaporation and/or extraction processes.

The preparation of a large number of per-O-benzylated oligosaccharides has been described in scientific literature before but these oligosaccharide derivatives were rarely crystalline solids providing oils or syrups of hydrated derivatives. However, the present invention provides numerous examples when even simple O-benzylated novel oligosaccharides give crystalline solids due to careful structural designs such as controlling anomeric purities and/or creating apolar molecular regions by the introduction of multiple O-benzyl moieties into the most advanced oligosaccharide intermediates. On the other hand the present invention also utilises the high crystalline properties of oligosaccharide intermediates decorated with selected substituted O-benzyl protecting groups.

The combination of using hydrogenolysis of highly crystalline O-benzylated and/or substituted O-benzylated oligosaccharide intermediates creates the very base of potential oligosaccharide manufacturing technologies.

As stated above, many oligosaccharides give oils or syrups limiting manufacturing purification technologies to expensive chromatographies. The high water solubility and low organic solvent solubility of unprotected oligosaccharides further narrow the scopes of purification technologies to high cost reverse phase separations. The present invention provides an alternative low cost purification protocol for the preparation of unprotected oligosaccharides in high purities by converting crude oligosaccharide mixtures into crystalline O-benzylated/substituted O-benzylated oligosaccharides first, using crystallisation as a low cost purification tool in the second stage and removing the O-benzyl/substituted O-benzyl protecting groups in the final stage.

In fact, the present invention combines the highly advantageous features of hydrogenolysis, and the high crystalline properties of O-benzylated/substituted O-benzylated oligosaccharide intermediates.

The first aspect of the present invention relates to the use of compounds of general formula 1 for the preparation of 2'-O-fucosyllactose, characterized in that a compound of general formula 1

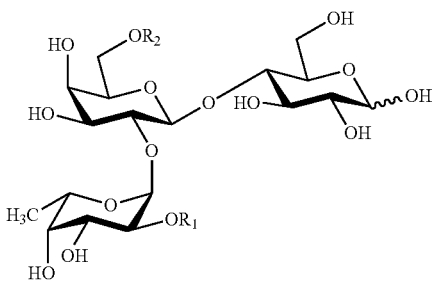

1 wherein $R_1$ is a group removable by hydrogenolysis and $R_2$ is a group removable by hydrogenolysis or H—or a hydrate or solvate thereof is subjected to catalytic hydrogenolysis.

The term "a group removable by hydrogenolysis" refers to groups whose bond coupled to the oxygen splits easily by addition of hydrogen in the presence of palladium, Raney nickel or an appropriate metal catalyst resulting in the regeneration of the protected one or more OH-groups. This kind of protective groups is well-known to the person skilled in the art, many of them are referred to by P. G. M. Wuts and T. W. Greene: *Protective groups in organic synthesis* John Wiley & Sons (2007), including but not limited to benzyl, diphenylmethyl (benzhydryl), 1-naphthylmethyl, 2-naphthylmethyl, benzyloxymethyl, benzyloxycarbonyl or triphenylmethyl (trityl) groups, all of them may be optionally substituted by one or more alkyl, alkoxy, phenyl, amino, acylamino, alkylamino, dialkylamino, nitro, carboxyl, alkoxycarbonyl, carbamoyl, N-alkylcarbamoyl, N,N-dialkylcarbamoyl, azido, halogenalkyl or halogene on the aromatic ring(s).

The term "catalytic hydrogenolysis" intends to mean reduction with hydrogen in the presence of a catalyst that typically takes place in a protic solvent or in a mixture of protic solvents. A protic solvent may be selected from a group consisting of water, acetic acid or $C_1$-$C_6$ alcohol. Mixture of one or more protic solvents with one or more proper aprotic organic solvents miscible partially or fully with the protic solvent(s) (such as THF, dioxane, ethyl acetate, acetone, etc.) may also be applied. Water, one or more $C_1$-$C_6$ alcohols or a mixture of water and one or more $C_1$-$C_6$ alcohols are preferably used as solvent system. Solutions containing the carbohydrate derivatives any concentration and suspensions of the carbohydrate derivatives with the solvent(s) used are also applicable. The reaction mixture is stirred at 10-100° C. temperature range, preferably between 20-50° C. in hydrogen atmosphere of 1-50 bar in the presence of a catalyst such as palladium, Raney nickel or any other appropriate metal catalyst, preferably palladium on charcoal or palladium black, until reaching the completion of the reaction. Catalyst metal concentrations generally range from 0.1% to 10% based on the weight of carbohydrate. Preferably, the catalyst concentrations range from 0.15% to 5%, more preferably 0.25% to 2.25%. Transfer hydrogenation may also be performed, when the hydrogen is generated in situ from cyclohexene, cyclohexadiene, formic acid or ammonium formate. The pH of the hydrogenolysis mixture is preferably neutral but organic or inorganic bases/acids and/or basic and/or acidic ion exchange resins can also be used to improve the kinetics of the hydrogenolysis. The use of basic substances is especially preferred when halogen substituents are present on the substituted benzyl moieties of the precursors. Organic acid is favourably used as a co-solvent or additive in cases when multiple benzyl groups have to be removed from the precursors. Preferred organic bases are including but not limited to triethylamine, diisopropyl ethylamine, ammonia, ammonium carbamate, diethylamine, etc. Preferred organic acids are including but not limited to formic acid, acetic acid, propionic acid, chloroacetic acid, dichloroacetic acid, trifluoroacetic acid, etc. The conditions proposed allow studying scale-up procedures and developing industrial method for producing 2'-FL. In addition, a simple, convenient and delicate removal of the solvent(s) can be applied giving rise to 2'-FL in excellent yield and high purity.

In one preferred embodiment 2'-O-fucosyllactose produced by methodologies of the present invention can be isolated as an amorphous solid by precipitation from water/organic solvent/aqueous solutions by cooling or by the addition of ethers including but not limited to MTBE, diethyl ether, diisopropyl ether etc. and/or $C_1$-$C_6$ alcohols. Alternatively 2'-O-fucosyllactose can also be isolated by freeze drying and spray drying.

In one preferred embodiment the hydrogenolysis of compounds characterized by general formula 1 is conducted in neutral conditions using water or water-alcohol mixture as a solvent, 2-10% palladium on charcoal or palladium black as a catalyst in 1-10 atm of hydrogen pressure at 20-60° C. temperature. After the completion of the hydrogenolysis, the reaction mixture is filtered and preferably concentrated by removing the organic solvent components and subjected to precipitation, spray drying, freeze drying producing anhydrous and/or hydrated 2'-O-fucosyllactose (water content 0-20%) in a controlled manner.

In another preferred embodiment the hydrogenolysis of compounds characterized by general formula 1 is conducted in neutral conditions using water or water-alcohol mixture as a solvent, 2-10% palladium on charcoal or palladium black as a catalyst in 1-10 atm of hydrogen pressure at 20-60° C. temperature. After the completion of the hydrogenolysis, the reaction mixture is filtered and preferably concentrated producing 2'-O-fucosyllactose aqueous solutions/syrup with a 2'-O-fucosyllactose concentration of 10-95%.

According to a preferred realization of the invention a compound of general formula 1, wherein $R_1$ is benzyl, 4-methylbenzyl, naphthylmethyl, benzyloxycarbonyl, 4-phenylbenzyl, 4-chlorobenzyl, 4-methoxybenzyl, 3,4-dimethoxybenzyl, 2,4,6-trimethylbenzyl or 2,3,4,5,6-pentamethylbenzyl, more preferably benzyl or 4-methylbenzyl and $R_2$ is H, is used in the hydrogenolysis.

Both solid forms of 2'-O-fucosyllactose such as amorphous/freeze dried/spray dried/and liquid forms of 2'-O-fucosyllactose such as aqueous solutions/syrups provided by the present invention have high 2'-FL purity suitable for infant nutritional use including but not limited to infant formulas, infant cereals, clinical infant nutritional products etc. In general, both solid and liquid forms of 2'-O-fucosyllactose produced by the methodologies of the present invention are suitable for general nutritional use for infants, toddlers, children, adults and elderly. Both solid and liquid forms of 2'-O-fucosyllactose provided by the present invention can also be used as food additives, dietary supplements, a component of alcoholic and non alcoholic beverages such as soft drinks, fruit juices, bottled water, wine, beer etc. Both solid and liquid forms of 2'-O-fucosyllactose provided by the present invention can also be used as a therapeutic agent in broad therapeutic application areas including but not limited to prevent bacterial and viral infections, to avoid diarrhea, to enhance immune system and brain development, etc. Both solid and liquid forms of 2'-O-fucosyllactose provided by the present invention can also be used in veterinary applications including but not limited to fight against infectious diseases of domesticated animals. 2'-O-fucosyllactose provided by the present invention can also be used as a crucial monomer for the preparation of polymeric/polymer mounted products providing multivalent binding for bacteria and viruses. 2'-O-fucosyllactose provided by the present invention can also be used for the preparation of other human milk oligosaccharides by applying chemical and/or enzymatic methodologies including but not limited to simple structural modifications of further fucosylation, further sialylation, further extension of the core structure via N-acetyl lactosaminylation/N-acetyl-isolactosamination, etc.

The second aspect of the present invention provides novel trisaccharides characterized by general formula 1

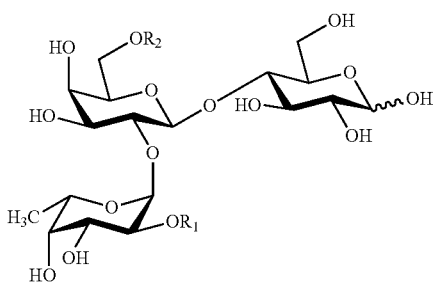

wherein $R_1$ is a group removable by hydrogenolysis and $R_2$ is a group removable by hydrogenolysis or H—or a hydrate or solvate thereof.

It is strongly emphasised that novel derivatives characterized by general formula 1 can be considered as sole chemical entities such as either α or β anomers or even an anomeric mixture of α and β isomers. Novel 2'-O-fucosyllactose intermediates of general formula 1 can be characterized as crystalline solids, oils, syrups, precipitated amorphous material or spray dried products. If crystalline, compounds of general formula 1 might exist either in anhydrous or in hydrated crystalline forms by incorporating one or several molecules of water into their crystal structures. Similarly, novel compounds characterized by general formula 1 might exist as crystalline substances incorporating ligands such as organic molecules and/or ions into their crystal structures.

In one preferred embodiment the novel trisaccharide is characterized by general formula 1 when $R_1$ is benzyl, 4-methylbenzyl, benzyloxycarbonyl, naphthylmethyl, 4-phenylbenzyl, 4-chlorobenzyl, 4-methoxybenzyl, 3,4-dimethoxybenzyl, 2,4,6-trimethylbenzyl or 2,3,4,5,6-pentamethylbenzyl, more preferably benzyl or 4-methylbenzyl and $R_2$ is H.

Novel compounds of general formula 1 provided by the present invention can be used for the preparation of 2'-O-fucosyllactose itself and other 2'-O-fucosyllactose derivatives by using chemical/enzymatic methodologies known in Art. Novel compounds of general formulas 1 can also be used as advanced precursors/intermediates for the production/preparation of numerous human milk oligosaccharides. Novel compounds of general formulas 1 can also be considered as valuable intermediates for the synthesis of complex oligosaccharides/glycoconjugates suitable for therapeutic/nutritional use.

The third aspect of the present invention relates to a method for the preparation of compounds of general formula 1, characterized in that a compound of general formula 2

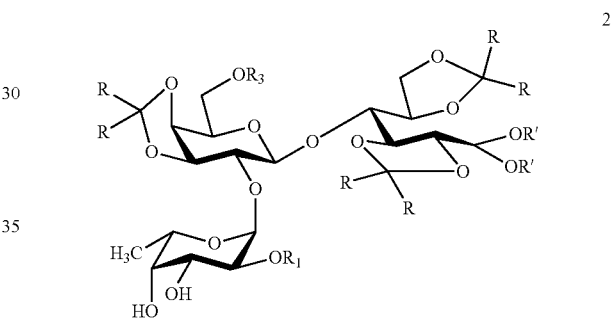

wherein $R_1$ is a group removable by hydrogenolysis, $R_3$ is a group removable by hydrogenolysis, acetal type group, silyl group or H, R is alkyl or two geminal R-groups with the carbon atom to which they are attached form a $C_3$-$C_6$ cycloalkyl ring, R' is alkyl—or a hydrate or solvate thereof is subjected to acid catalyzed mild hydrolysis.

The term "acetal type group" means protective groups that with the oxygen atom of the hydroxyl group to be protected form a structure with two single bonded oxygens attached to the same carbon atom characterized by the following general structure:

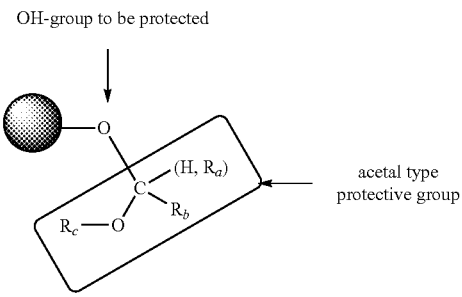

wherein $R_a$, $R_b$ and $R_c$ are carbon-bonded groups. This kind of groups is well-known to the person skilled in the art, many of them are referred to by P. G. M. Wuts and T. W. Greene: *Protective groups in organic synthesis* John Wiley & Sons (2007), including but not limited to methoxymethyl, t-butoxymethyl, 2-methoxy-ethoxymethyl, benzyloxymethyl, tetrahydropyranyl, tetrahydrofuranyl, 1,4-dioxan-2-yl, 1-methyl-1-methoxyethyl, 1-methyl-1-phenoxyethyl, etc. The acetal type protective groups are labile under mild acidic conditions.

The term "silyl group" means a protective group containing silicon atom covalently bonded to the oxygen atom of a hydroxy group to be protected (silyl ethers). This kind of groups is well-known to the person skilled in the art, many of them are referred to by P. G. M. Wuts and T. W. Greene: *Protective groups in organic synthesis* John Wiley & Sons (2007), including but not limited to trimethylsilyl, triisopropylsilyl, t-butyldimethylsilyl, t-butyldiphenylsilyl, etc. The silyl ethers are labile under mild acidic conditions.

The term "acid catalyzed mild hydrolysis" refers to a chemical reaction in which water reacts in the presence of acid at pH>2 with another substance bearing acid labile protective group(s) to regenerate the functional group(s) protected. In the present context the acid labile protective groups may be protective groups of primary or secondary hydroxyls (in the form of acyclic acetals or silyl ethers), 1,2-diol systems (in the from of cyclic acetals) or a formyl group (in the form of acetals). The starting compound may bear more than one acid labile protective groups that may be removed simultaneously or successively. In addition, the starting compound may contain acyl protective groups as well. The skilled person is fully aware that acyl groups can be deprotected by only strong acidic hydrolysis (pH<2). The skilled person is able to distinguish which deprotective condition affects the acetal and/or silyl groups while the acyl groups remain intact. Furthermore the interglycosidic linkages may be also sensitive to acids. The skilled person is fully aware that interglycosidic linkages can be splitted by only strong acidic hydrolysis (pH<2). The skilled person is able to distinguish which deprotective condition affects the acetal and/or silyl groups while the interglycosidic linkages remain intact. Water—which has to be present in the reaction milieu as reagent—may serve as solvent or co-solvent as well. Organic protic or aprotic solvents which are stable under acidic conditions and miscible fully or partially with water such as $C_1$-$C_6$ alcohols, acetone, THF, dioxane, ethyl acetate, MeCN, etc. may be used in a mixture with water. The acids used are generally protic acids selected from but not limited to acetic acid, trifluoroacetic acid, HCl, formic acid, sulphuric acid, perchloric acid, oxalic acid, p-toluenesulfonic acid, benzenesulfonic acid, cation exchange resins, etc., which may be present in from catalytic amount to large excess. The hydrolysis may be conducted at temperatures between 20° C. and reflux until reaching completion which takes from about 2 hours to 3 days depending on temperature, concentration and pH. Preferably, organic acids including but not limited to aqueous solutions of acetic acid, formic acid, chloroacetic acid, oxalic acid, etc. are used at 40-75° C. Another preferred condition is to use a $C_1$-$C_6$ alcohol-acetonitrile or $C_1$-$C_6$ alcohol-water mixture in the presence of HCl or sulfonic acids such as p-toluenesulfonic acid or camphorsulfonic acid.

Alternatively, anhydrous $C_1$-$C_6$ alcohol including but not limited to methanol, ethanol, propanol, butanol, etc. can also be used for the required cleavage of the acyclic/cyclic acetal/ketal moieties via acid catalyzed trans-acetalization/transketalization processes. Catalytic amount of hydrogen chloride, sulphuric acid, perchloric acid, p-toluenesulfonic acid, acetic acid, oxalic acid, camphorsulfonic acid, strong acidic ion-exchange resins, etc. can be used for the purposes at temperatures of 20° C. to reflux.

In a preferred embodiment the acid catalyzed mild hydrolysis is carried out in a mixture of water and one or more $C_1$-$C_6$ alcohols in the presence of a sulfonic acid, preferably in water-isopropanol mixture in the presence of p-toluenesulfonic acid.

In a preferred embodiment a compound characterized by general formula 2, wherein $R_1$ is benzyl, 4-methylbenzyl, naphthylmethyl, benzyloxycarbonyl, 4-phenylbenzyl, 4-chlorobenzyl, 4-methoxybenzyl, 3,4-dimethoxybenzyl, 2,4,6-trimethylbenzyl or 2,3,4,5,6-pentamethylbenzyl, more preferably benzyl or 4-methylbenzyl, $R_3$ is H, and R and R' are methyl, is applied.

The fourth aspect of the present invention provides novel oligosaccharide derivatives characterized by general formula 2

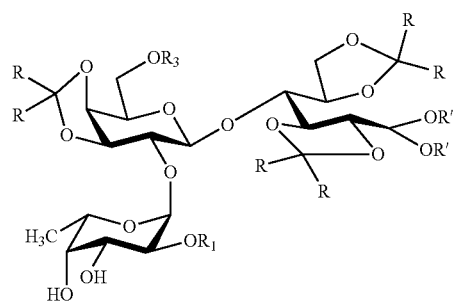

wherein $R_1$ is a group removable by hydrogenolysis, $R_3$ is a group removable by hydrogenolysis, acetal type group, silyl group or H, R is alkyl or two geminal R-groups with the carbon atom to which they are attached form a $C_3$-$C_6$ cycloalkyl ring, R' is alkyl, or a hydrate or solvate thereof.

Novel 2'-O-fucosyllactose intermediates of general formula 2 can be characterized as crystalline solids, oils, syrups, precipitated amorphous material or spray dried products. If crystalline, compounds of general formula 2 might exist either in anhydrous or in hydrated crystalline forms by incorporating one or several molecules of water into their crystal structures. Similarly, novel compounds characterized by general formula 2 might exist as crystalline substances incorporating ligands such as organic molecules and/or ions into their crystal structures.

In one preferred embodiment the novel oligosaccharide is characterized by general formula 2 wherein $R_1$ is benzyl, 4-methylbenzyl, naphthylmethyl, benzyloxycarbonyl, 4-phenylbenzyl, 4-chlorobenzyl, 4-methoxybenzyl, 3,4-dimethoxybenzyl, 2,4,6-trimethylbenzyl or 2,3,4,5,6-pentamethylbenzyl, more preferably benzyl or 4-methylbenzyl, $R_3$ is H, and R and R' both are methyl.

Novel compounds of general formula 2 provided by the present invention can be used for the preparation of 2'-O-fucosyllactose and other 2'-O-fucosyllactose derivatives by using chemical/enzymatic methodologies known in Art. Novel compounds of general formulas 2 can also be used as advanced precursors/intermediates for the production/preparation of numerous human milk oligosaccharides. Novel compounds of general formulas 2 can also be considered as valuable intermediates for the synthesis of complex oligosaccharides/glycoconjugates suitable for therapeutic/nutritional use.

The fifth aspect of the present invention is related to a method for the preparation of compounds of general formula 1 comprising deacylation of compounds of general formula 3

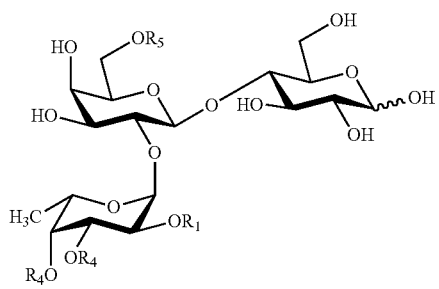

wherein $R_1$ is a group removable by hydrogenolysis, $R_4$ is optionally substituted acyl, $R_5$ is a group removable by hydrogenolysis or optionally substituted acyl, or a hydrate or solvate thereof.

The term "deacylation" means removing O-acyl protective groups. A manner to deacylate may be base catalyzed transesterification deprotection that is the acyl protective groups from hydroxyls are removed in an alcohol solvent such as methanol, ethanol, propanol, t-butanol, etc. in the presence of an alcoholate like NaOMe, NaOEt, KO$^t$Bu, etc. at 20-100° C. temperatures. The alcohol and the alcoholate should be matched. The use of co-solvent as toluene or xylene might be beneficial in order to control particle size of the product and to avoid gel formations. In a preferred embodiment catalytic amount of NaOMe is used in methanol or in methanol-toluene mixture at 40-60° C. (Zemplén deacylation). A further way to deacylate may be basic hydrolysis which generally means base catalyzed hydrolysis in water, alcohol or water-organic solvent mixtures, in homogeneous or heterogeneous reaction conditions at temperatures varying from 0-100° C. The base of choice is generally a strong base, e.g. LiOH, NaOH, KOH, Ba(OH)$_2$, K$_2$CO$_3$, basic ion exchange resins, tetraalkylammonium hydroxides, etc. The bases can be used in the form of an aqueous solution as well. In a preferred embodiment the base is NaOH and the solvent is methanol. An alternative way to deacylate may be aminolysis (N-acyl transfer based deprotection) which means a treatment with ammonia, hydrazine, substituted hydrazine, ethylene diamine or primary amines in water, alcohol or water-organic solvent mixtures at 20-120° C. temperatures. Under either conditions for deacylating mentioned above the acid labile protective groups or interglycosidic linkages are not affected.

In according to more preferred conditions, a compound of general formula 3, wherein $R_1$ is defined as benzyl, 4-methylbenzyl, naphthylmethyl, benzyloxycarbonyl, 4-phenylbenzyl, 4-chlorobenzyl, 4-methoxybenzyl, 3,4-dimethoxybenzyl, 2,4,6-trimethylbenzyl or 2,3,4,5,6-pentamethylbenzyl, more preferably benzyl or 4-methylbenzyl, $R_4$ is benzoyl or 4-chlorobenzoyl and $R_5$ is pivaloyl, benzoyl or 4-chlorobenzoyl, is deacylated in methanol in the presence of NaOMe or NaOH.

The sixth aspect of the present invention provides novel oligosaccharide derivatives characterized by general formula 3

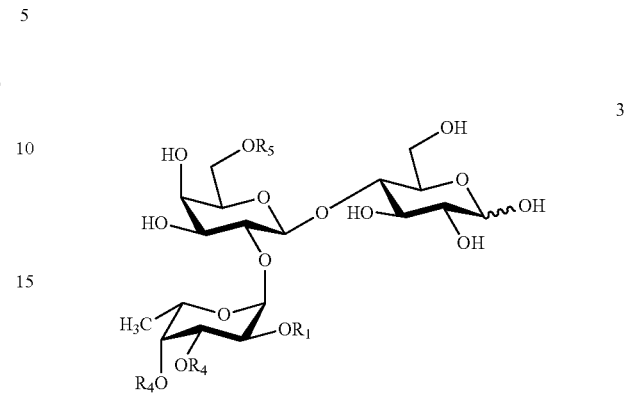

wherein $R_1$ is a group removable by hydrogenolysis, $R_4$ is optionally substituted acyl, $R_5$ is a group removable by hydrogenolysis or optionally substituted acyl, or a hydrate or solvate thereof.

It is strongly emphasised that novel derivatives characterized by general formula 3 can be considered as sole chemical entities such as either α or β anomers or even an anomeric mixture of α and β isomers. Novel 2'-O-fucosyllactose intermediates of general formula 3 can be characterized as crystalline solids, oils, syrups, precipitated amorphous material or spray dried products. If crystalline, compounds of general formula 3 might exist either in anhydrous or in hydrated crystalline forms by incorporating one or several molecules of water into their crystal structures. Similarly, novel compounds characterized by general formula 3 might exist as crystalline substances incorporating ligands such as organic molecules and/or ions into their crystal structures.

In a preferred embodiment the novel oligosaccharide is characterized by general formula 3 wherein $R_1$ is defined as benzyl, 4-methylbenzyl, naphthylmethyl, benzyloxycarbonyl, 4-phenylbenzyl, 4-chlorobenzyl, 4-methoxybenzyl, 3,4-dimethoxybenzyl, 2,4,6-trimethylbenzyl or 2,3,4,5,6-pentamethylbenzyl, more preferably benzyl or 4-methylbenzyl, $R_4$ denotes benzoyl optionally substituted by one or more halogens and $R_5$ means alkanoyl or benzoyl optionally substituted by one or more halogens. In an even more preferred embodiment $R_1$ is benzyl or 4-methylbenzyl, $R_4$ is benzoyl or 4-chlorobenzoyl and $R_5$ is pivaloyl, benzoyl or 4-chlorobenzoyl.

Novel compounds of general formula 3 provided by the present invention can be used for the preparation of 2'-O-fucosyllactose and other 2'-O-fucosyllactose derivatives by using chemical/enzymatic methodologies known in Art. Novel compounds of general formulas 3 can also be used as advanced precursors/intermediates for the production/preparation of numerous human milk oligosaccharides. Novel compounds of general formulas 3 can also be considered as valuable intermediates for the synthesis of complex oligosaccharides/glycoconjugates suitable for therapeutic/nutritional use.

The seventh aspect of the present invention relates to a method for the preparation of compounds of general formula 2 comprising deacylation of compounds of general formula 4

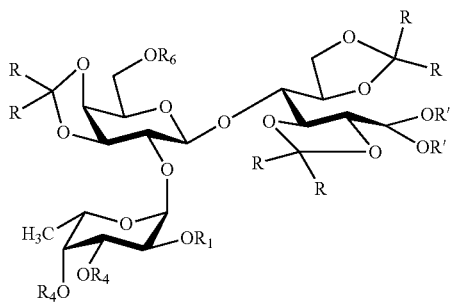

wherein $R_1$ is a group removable by hydrogenolysis, $R_4$ is optionally substituted acyl, $R_6$ is a group removable by hydrogenolysis, acetal type group, silyl group or optionally substituted acyl, R is alkyl or two geminal R-groups with the carbon atom to which they are attached form a $C_3$-$C_6$ cycloalkyl, R' is alkyl, or a hydrate or solvate thereof.

In according to more preferred conditions, a compound of general formula 4, wherein $R_1$ is defined as benzyl, 4-methylbenzyl, naphthylmethyl, benzyloxycarbonyl, 4-phenylbenzyl, 4-chlorobenzyl, 4-methoxybenzyl, 3,4-dimethoxybenzyl, 2,4,6-trimethylbenzyl or 2,3,4,5,6-pentamethylbenzyl, more preferably benzyl or 4-methylbenzyl, $R_4$ is benzoyl or 4-chlorobenzoyl, $R_6$ is pivaloyl, benzoyl or 4-chlorobenzoyl, and R and R' is methyl, is deacylated in methanol in the presence of NaOMe or NaOH.

The eighth aspect of the present invention relates to a method for the preparation of compounds of general formula 3

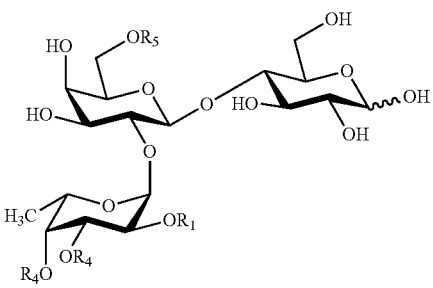

wherein $R_1$ is a group removable by hydrogenolysis, $R_4$ is optionally substituted acyl, $R_5$ is a group removable by hydrogenolysis or optionally substituted acyl—comprising acid catalyzed mild hydrolysis of compounds of general formula 4

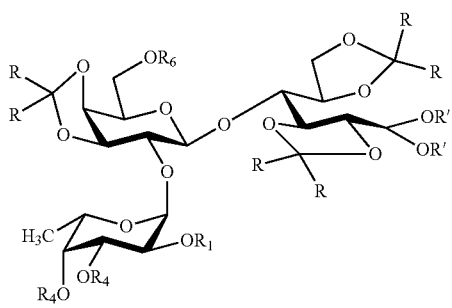

wherein $R_1$ is a group removable by hydrogenolysis, $R_4$ is optionally substituted acyl, $R_6$ is a group removable by hydrogenolysis, acetal type group, silyl group or optionally substituted acyl, R is alkyl or two geminal R-groups with the carbon atom to which they are attached form a $C_3$-$C_6$ cycloalkyl, R' is alkyl, or a hydrate or solvate thereof.

In according to a preferred embodiment, a compound of general formula 4, wherein $R_1$ is defined as benzyl, 4-methylbenzyl, naphthylmethyl, benzyloxycarbonyl, 4-phenylbenzyl, 4-chlorobenzyl, 4-methoxybenzyl, 3,4-dimethoxybenzyl, 2,4,6-trimethylbenzyl or 2,3,4,5,6-pentamethylbenzyl, more preferably benzyl or 4-methylbenzyl, $R_4$ is benzoyl or 4-chlorobenzoyl, $R_6$ is pivaloyl, benzoyl or 4-chlorobenzoyl, and R and R' is methyl, is hydrolyzed in aqueous acetonitrile or in aqueous acetone in the presence of p-toluenesulphonic acid or HCl.

The ninth aspect of the present invention provides novel oligosaccharide derivatives characterized by general formula 4

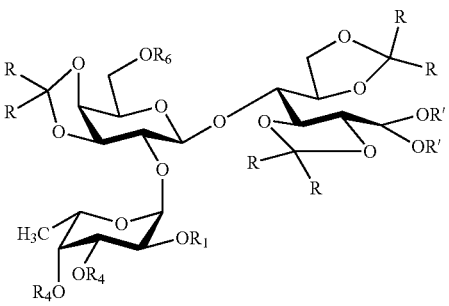

wherein $R_1$ is a group removable by hydrogenolysis, $R_4$ is optionally substituted acyl, $R_6$ is a group removable by hydrogenolysis, acetal type group, silyl group or optionally substituted acyl, R is alkyl or two geminal R-groups with the carbon atom to which they are attached form a $C_3$-$C_6$ cycloalkyl, R' is alkyl, or a hydrate or solvate thereof.

Novel 2'-O-fucosyllactose intermediates of general formula 4 can be characterized as crystalline solids, oils, syrups, precipitated amorphous material or spray dried products. If crystalline, compounds of general formula 4 might exist either in anhydrous or in hydrated crystalline forms by incorporating one or several molecules of water into their crystal structures. Similarly, novel compounds characterized by general formula 4 might exist as crystalline substances incorporating ligands such as organic molecules and/or ions into their crystal structures.

In one preferred embodiment the novel oligosaccharide is characterized by general formula 4 wherein $R_1$ defined as benzyl, 4-methylbenzyl, naphthylmethyl, benzyloxycarbonyl, 4-phenylbenzyl, 4-chlorobenzyl, 4-methoxybenzyl, 3,4-dimethoxybenzyl, 2,4,6-trimethylbenzyl or 2,3,4,5,6-pentamethylbenzyl, more preferably benzyl or 4-methylbenzyl, $R_4$ denotes benzoyl optionally substituted by one or more halogens, $R_6$ means alkanoyl or benzoyl optionally substituted by one or more halogens, and R and R' is methyl. In an even more preferred embodiment $R_1$ is benzyl or 4-methylbenzyl, $R_4$ is benzoyl or 4-chlorobenzoyl and $R_6$ is pivaloyl, benzoyl or 4-chlorobenzoyl.

Novel compounds of general formula 4 provided by the present invention can be used for the preparation of 2'-O-fucosyllactose and other 2'-O-fucosyllactose derivatives by using chemical/enzymatic methodologies known in Art. Novel compounds of general formulas 4 can also be used as advanced precursors/intermediates for the production/preparation of numerous human milk oligosaccharides. Novel compounds of general formulas 4 can also be considered as valuable intermediates for the synthesis of complex oligosaccharides/glycoconjugates suitable for therapeutic/nutritional use.

The tenth aspect of the present invention relates to a method for the preparation of compounds of general formula 4 comprising the coupling reaction of a donor compound of general formula 5

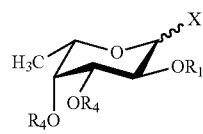
5 wherein $R_1$ and $R_4$ are defined above and X is halogen, —OC(=NH)CCl$_3$, —O-pentenyl, —OAc, —OBz or —SR$_7$, in which R$_7$ is alkyl or optionally substituted phenyl—with an acceptor compound of general formula 6

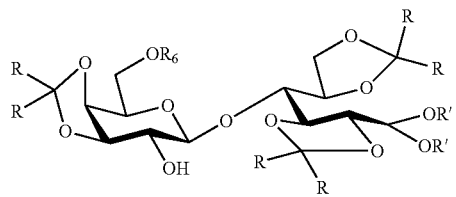
6 wherein R, R' and $R_6$ are defined above—under glycosylation condition.

The term "glycosidation condition" means in the present context to run the reaction in an aprotic solvent or in a mixture of aprotic solvents in the presence of an activator so as to lead to the desired glycosylated product by controlling the stereoselectivity of the conjugation via non-neighbouring group active protecting group strategy, solvent effect, halide effect, promoter selection and temperature control. In case of carbohydrates an array of anomeric activation for glycosylation is developed and available to a skilled person engaged in synthetic carbohydrate chemistry. These methodologies are expansively discussed by reviews and handbooks, for instance by Demchenko (Ed.): *Handbook of Chemical Glycosylation* Wiley (2008). For the sake of examples some general considerations are briefly mentioned below depending on the X-group (the protecting groups of the acceptors and donors remain intact under glycosylation).

The glycosyl halides (X means F, Cl, Br, I) are frequently used in glycosylation reaction because of their easy accessibility and satisfactory reactivity. Typically, anomeric halides follow the reactivity order F<Cl<Br<I for nucleophilic displacement. The glycosylation reactions are generally promoted by heavy metal ion, mainly mercury or silver, and Lewis acids. The glycosyl fluorides may be prepared by treatment of the appropriate precursors such as hemiacetals, glycosyl halides, glycosyl esters and S-glycosides with fluorinating reagents such as HF, AgF, AgBF$_4$, tetrabutyl ammonium fluoride, diethylaminosulfur trifluoride, 2-fluoro-1-methylpyridinium tosylate, Selectfluor, Deoxo-Fluor, 4-methyl(difluoroiodo)benzene, etc.

Glycosyl trichloroacetimidates (X=—OC(=NH)CCl$_3$) can be easily prepared by the addition of the free anomeric OH to trichloroacetonitrile under inorganic or organic base catalysis. In a typical glycosidation reaction catalytic amount of Lewis acid, such as trimethylsilyl triflate or BF$_3$-etherate, promotes the coupling.

Glycosyl acetates or benzoates (X represents —OAc or —OBz) in glycosylation reaction are first subjected to electrophilic activation providing a reactive intermediate, then treated with the nucleophilic OH-acceptor. Typical activators of choice are Bronsted acids (such as p-TsOH, HClO$_4$, sulfamic acid), Lewis acids (such as ZnCl$_2$, SnCl$_4$, triflate salts, BF$_3$-etherate, trityl perchlorate, AlCl$_3$, triflic anhydride) and their mixtures.

Pentenyl glycosides (X means —O—(CH$_2$)$_3$—CH=CH$_2$) as glycosyl donors can be transglycosylated with appropriate glycosyl acceptors in the presence of a promoter such as NBS and NIS. Protic or Lewis acids (triflic acid, Ag-triflate, etc.) may enhance the reaction. The pentenyl glycosides can be prepared with the aid of n-pentenol by standard Fischer glycosylation of hemiacetals under acidic condition, by silver(I) salt promoted coupling of glycosyl bromides (Koenigs-Knorr method), or by glycosylation of 1-acetyl glycosides in the presence of tin(IV) chloride.

Thioglycosides (X denotes alkylthio- or optionally substituted phenylthio-group) can be activated by thiofilic promoters such as mercury(II) salts, Br$_2$, I$_2$, NBS, NIS, triflic acid, triflate salts, BF$_3$-etherate, trimethylsilyl triflate, dimethylmethylthio sulphonium triflate, phenylselenyl triflate, iodonium dicollidine perchlorate, tetrabutylammonium iodide or mixtures thereof, in condensation reactions, preferably by Br$_2$, NBS, NIS or triflic acid.

In a preferred method the glycosyl donor of choice is a compound of general formula 5

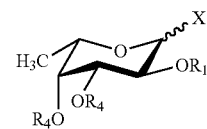
5 wherein $R_1$ is a group removable by hydrogenolysis, $R_4$ is optionally substituted acyl and X is phenylthio optionally substituted with one or more alkyl, more preferably $R_1$ is benzyl, 4-methylbenzyl, naphthylmethyl, benzyloxycarbonyl, 4-phenylbenzyl, 4-chlorobenzyl, 4-methoxybenzyl, 3,4-dimethoxybenzyl, 2,4,6-trimethylbenzyl or 2,3,4,5,6-pentamethylbenzyl, $R_4$ denotes benzoyl optionally substituted by one or more halogens and X is unsubstituted phenylthio, even more preferably $R_1$ is benzyl or 4-methylbenzyl and $R_4$ is benzoyl or 4-chlorobenzoyl.

In a further preferred method the glycosyl acceptor of choice is a compound of general formula 6, wherein R and R' are methyl, and $R_6$ is pivaloyl, benzoyl or 4-chlorobenzoyl.

The glycosylation reaction runs in aprotic solvents such as toluene, THF, DCM, chloroform, dioxane, acetonitrile, chlorobenzene, ethylene dichloride, DMSO, DMF, N-methylpyrrolidone, etc. or mixtures thereof, preferably THF, toluene, DCM or mixtures thereof, more preferably in THF-DCM mixture at −20-20° C., preferably at −10-0° C. For thiophilic activation Br$_2$, NBS or NIS are employed, preferably in the presence of triflic acid. Usually a slight excess of donor (1.1-1.2 eq) is used compared to the acceptor. Reaction time alters from 5 min to 2 hours. For quenching the reaction water or alcohols are generally employed, preferably aqueous or alcoholic solutions of bases like ammonia or triethyl amine, more preferably 25% ammonium hydroxide.

The synthesis of acceptors of general formula 6 can be carried out by known manner. Treatment of lactose with dialkoxy ketal of a symmetric ketone at reflux in the presence of acid such as p-toluenesulfonic acid gives rise to 2,3:5,6-di-O-alkylidene-4-O-(3,4-O-alkylidene-β-D-galactopyranosyl)-D-glucose dialkyl acetal. The selective 6'-O-substitution of the primary hydroxyl group of lactose ketonide diol can be achieved for example with base catalysed reactions including $R_1$-halides to give compounds of general formula 6 wherein $R_6$ is a group removable by hydrogenolysis. Both inorganic and organic bases including but not limited to sodium hydride, potassium tert-butoxide, potassium hydroxide, sodium hydroxide, potassium carbonate, diisopropyl ethylamine, 1,8-diazabicyclo[5.4.0]undec-7-enc are suitable to catalyse such selective 6'-O-substitution processes of lactose ketonide diol. Such reactions can be performed either in homogeneous solutions using solvents such as DMF, THF, dioxane etc. or in aqueous phase transfer alkylation conditions. Preferably, NaH or potassium tert-butoxide is used in dioxane or DMF at 20-80° C. The selective 6-O-acylation can be conducted with traditional acylating agents like acyl halides, anhydrides, active esters, etc. in the presence of pyridine, triethylamine, diisopropyl ethylamine using organic solvents such as DCM, chloroform, THF, dioxane, acetonitrile, etc. or mixture thereof at −20-80° C. to yield compounds of general formula 6 wherein $R_6$ is acyl. Selective acyclic acetal formation of lactose acetonide diol on the 6'-position can be performed with for example methoxymethyl, t-butoxymethyl, 2-methoxyethyl, benzyloxymethyl, 2-tetrahydrofuranyl halogenides, etc. in the presence of triethylamine, morpholine, diisopropyl ethylamine, pyridine, etc., or with for example dihydropyran, 1,4-dihydrodioxin, dihydrofuran, 2-methoxypropene, 2-phenoxypropene, etc. in the presence of acids in organic solvents such as DMF, THF, dioxane, acetonitrile, etc. at 0-60° C. temperature to give rise to compounds of general formula 6 wherein $R_6$ is acetal type group. Selective primary OH-silylation reaction of the lactose acetonide diol with a silyl chloride in the presence of an amine base (such as imidazole, triethyl amine, etc.) at room temperature or with a silyl triflate with a hindered amine base (e.g. 2,6-lutidine) at low temperature can lead to compounds of general formula 6 wherein $R_6$ is silyl.

The eleventh aspect of the present invention to provide compounds of general formula 7 belonging to general formula 5

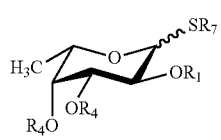

7 wherein $R_1$ is a group removable by hydrogenolysis, $R_4$ is acyl and $R_7$ is alkyl or optionally substituted phenyl, with the proviso that phenyl 3,4-di-O-acetyl-2-O-benzyl-1-thio-L-fucopyranoside, methyl 3,4-di-O-acetyl-2-O-benzyl-1-thio-L-fucopyranoside, ethyl 3,4-di-O-acetyl-2-O-benzyl-1-thio-L-fucopyranoside and ethyl 3,4-di-O-acetyl-2-O-(4-methoxybenzyl)-1-thio-L-fucopyranoside are excluded.

It is strongly emphasised that novel derivatives characterized by general formula 7 can be considered as sole chemical entities such as either α or β anomers or even an anomeric mixture of α and β isomers. Novel 2'-fucosyllactose intermediates of general formula 7 can be characterized as crystalline solids, oils, syrups, precipitated amorphous material or spray dried products. If crystalline, compounds of general formula 7 might exist either in anhydrous or in hydrated crystalline forms by incorporating one or several molecules of water into their crystal structures, which are removed by conventional methods before glycosylation. Similarly, novel compounds characterized by general formula 7 might exist as crystalline substances incorporating ligands such as organic molecules and/or ions into their crystal structures. If the organic molecules are alcohols, they are removed by conventional methods before glycosylation.

In one preferred embodiment the novel oligosaccharide is characterized by general formula 7 wherein $R_7$ is phenyl optionally substituted with one or more alkyl and the anomeric configuration is β, more preferably $R_1$ is benzyl, 4-methylbenzyl, 1-naphthylmethyl, benzyloxycarbonyl, 3-phenylbenzyl, 4-chlorobenzyl, 4-methoxybenzyl, 3,4-dimethoxybenzyl, 2,4,6-trimethylbenzyl or 2,3,4,5,6-pentamethylbenzyl, $R_4$ denotes benzoyl optionally substituted by one or more halogens and $R_7$ is unsubstituted phenyl, even more preferably $R_1$ is benzyl or 4-methylbenzyl and $R_4$ is benzoyl or 4-chlorobenzoyl.

Novel compounds of general formula 7 provided by the present invention can be used for the preparation of 2'-O-fucosyllactose and other 2'-O-fucosyllactose derivatives by using chemical/enzymatic methodologies known in Art. Novel compounds of general formulas 7 can also be used as advanced precursors/intermediates for the production/preparation of numerous human milk oligosaccharides. Novel compounds of general formulas 7 can also be considered as valuable intermediates for the synthesis of complex oligosaccharides/glycoconjugates suitable for therapeutic/nutritional use.

The twelfth aspect of the present invention provides a methodology suitable for the preparation of novel compounds of general formula 7, characterized in that a compound of general formula 8

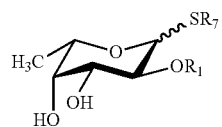

8 wherein $R_1$ is a group removable by hydrogenolysis and $R_7$ is alkyl or optionally substituted phenyl—is acylated by means of an acylating agent.

The term "acylating agent" intends to mean $R_4$-halogenides, an anhydride of general formula $(R_4)_2O$, active derivatives of carboxylic acid of formula $R_4$—OH such as imidazolide, thioester, silyl ester, vinyl ester, tetrazolide, orthoester, hydroxy-benztriazolyl ester, etc. or carboxylic acid of formula $R_4$—OH with suitable coupling reagents such as $Me_3SiCl$, DCC, BOP-Cl, TsCl/TEBAC, etc, wherein $R_4$ is optionally substituted acyl as defined above. Acylation can be conducted in the presence of pyridine, triethylamine, diisopropyl ethylamine, etc. in organic solvents such as DCM, chloroform, THF, dioxane, acetonitrile, etc. or mixture thereof at −20-80° C. Preferably acyl chlorides in a mixture of pyridine and DCM are used at 0-20° C., more preferably acyl is benzoyl or 4-chlorobenzoyl.

Compounds of general formula 8 are readily available by known methods in the art. L-Fucose is peracetylated then L-fucose tetraacetate is thiolized with $R_7SH$, wherein $R_7$ is defined above, in the presence of a Lewis acid to give optionally substituted phenyl 2,3,4-tri-O-acetyl-1-thio-β-L-fucopyranoside. Removal of the acetyl groups is achieved under Zemplén condition and the resulting triol is treated with dimethoxy-propane/acid to form the 3,4-acetonide. The free OH-group in the $2^{nd}$ position is then deprotonated with NaH and the alcoholate is reacted with $R_1$-halogenide wherein $R_1$ is defined above. Removal of the isopropylidene by means of acidic hydrolysis smoothly affords compounds of general formula 8.

The thirteen aspect of the present invention relates to a method for the preparation of 2'-O-fucosyllactose, characterized in that a compound of general formula 1

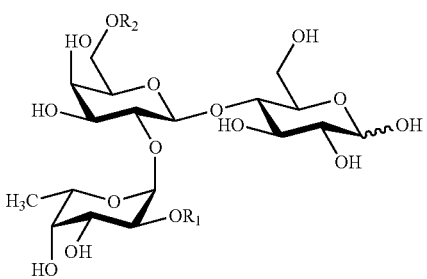

wherein $R_1$ is a group removable by hydrogenolysis and $R_2$ is a group removable by hydrogenolysis or H—or a hydrate or solvate thereof is subjected to catalytic hydrogenolysis.

In one preferred embodiment 2'-O-fucosyllactose produced by methodologies of the present invention can be isolated as an amorphous solid by precipitation from water/organic solvent/aqueous solutions by cooling or by the addition of ethers including but not limited to MTBE, diethyl ether, diisopropyl ether etc. and/or $C_1$-$C_6$ alcohols. Alternatively 2'-O-fucosyllactose can also be isolated by freeze drying and spray drying.

In one preferred embodiment the hydrogenolysis of compounds characterized by general formula 1 is conducted in neutral conditions using water or water-alcohol mixture as a solvent, 2-10% palladium on charcoal or palladium black as a catalyst in 1-10 atm of hydrogen pressure at 20-60° C. temperature. After the completion of the hydrogenolysis, the reaction mixture is filtered and preferably concentrated by removing the organic solvent components and subjected to precipitation, spray drying, freeze drying producing anhydrous and/or hydrated 2'-O-fucosyllactose (water content 0-20%) in a controlled manner.

In another preferred embodiment the hydrogenolysis of compounds characterized by general formula 1 is conducted in neutral conditions using water or water-alcohol mixture as a solvent, 2-10% palladium on charcoal or palladium black as a catalyst in 1-10 atm of hydrogen pressure at 20-60° C. temperature. After the completion of the hydrogenolysis, the reaction mixture is filtered and preferably concentrated producing 2'-O-fucosyllactose aqueous solutions/syrup with a 2'-O-fucosyllactose concentration of 10-95%.

According to a preferred realization of the invention a compound of general formula 1, wherein $R_1$ is benzyl, 4-methylbenzyl, naphthylmethyl, benzyloxycarbonyl, 4-phenylbenzyl, 4-chlorobenzyl, 4-methoxybenzyl, 3,4-dimethoxybenzyl, 2,4,6-trimethylbenzyl or 2,3,4,5,6-pentamethylbenzyl, more preferably benzyl or 4-methylbenzyl and $R_2$ is H, is used in the hydrogenolysis.

Other features of the invention will become apparent in the course of the following descriptions of exemplary embodiments which are given for illustration of the invention and are not to be limiting thereof.

EXPERIMENTAL

Example 1

4-O-(3,4-β-cyclohexylidene-β-D-galactopyranosyl)-2,3:5,6-di-O-cyclohexylidene-D-glucose dimethyl acetal Lactose (1.15 g) is suspended in cyclohexanone dimethoxy ketal (10 ml). p-Toluenesulfonic acid (45 mg) is added and the reaction mixture is heated to 85° C. for 2½ h. The mixture is then neutralized by addition of $Et_3N$, the solvent is concentrated in vacuo, the residue is dissolved in DCM (60 ml), the organic phase is washed with $H_2O$ (2×50 ml) and sat. $NaHCO_3$ (50 ml). Further purification is done by flash chromatography (EtOAc/heptane 6:4) giving the product (1.35 g, 64%) as a white foam.

$^1$H NMR (300 MHz, $CDCl_3$): δ=4.54 (dd, 1H, J=6.6, 7.9), 4.42 (d, 1H, J=8.3), 4.35 (m, 1H), 4.34 (d, 1H, J=6.6), 4.26 (dd, 1H, J=5.3, 8.7), 4.09-3.92 (5H), 3.87 (dd, 1H, J=1.3, 7.9), 3.80 (m, 1H), 3.65 (m, 1H), 3.49 (m, 1H), 3.48 and 3.47 (2s, each 3H), 1.69-1.26 (m, 30H).
$^{13}$C NMR ($CDCl_3$, 75 MHz): δ=110.9, 110.3, 108.9, 107.2, 103.4, 79.0, 77.8, 77.5, 75.6, 75.1, 74.7, 74.4, 73.1, 63.9, 62.4, 57.4, 54.4, 37.8, 36.4, 35.8, 35.4, 34.9, 33.1, 25.2-23.6.

Example 2

4-O-(6-O-acetyl-3,4-β-cyclohexylidene-β-D-galactopyranosyl)-2,3:5,6-di-O-cyclohexylidene-D-glucose dimethyl acetal Compound of example 1 (0.526 g, 0.83 mmol) is dissolved in dry DCM (5 ml). Pyridine (0.4 ml, 5.0 mmol) is added and the mixture is cooled to −30° C. Acetyl chloride (0.07 ml, 0.98 mmol) dissolved in DCM (0.5 ml) is added in 10 min. The mixture is stirred for 1 h at −20° C. MeOH (1 ml) is added and the mixture is allowed to warm to room temperature. DCM (20 ml) is added and the mixture is washed with $H_2O$ (50 ml), cold aq. HCl (0.5 M, 30 ml), $H_2O$ (30 ml), $NaHCO_3$ (30 ml), then dried ($Na_2SO_4$), filtered and evaporated in vacuo. Purification by flash chromatography (heptane/EtOAc, 6:4) gives the product as a white foam (0.47 g, 85%).

$^1$H NMR ($CDCl_3$, 300 MHz) δ: 4.43-4.26 (6H, unresolved), 4.17 (1H, dd, J=7.1, 8.6), 4.13 (1H, dd, J=1.7, 1.7), 4.09-4.00 (3H, unresolved), 3.93 (1H, ddd, J=1.8, 4.6, 7.7), 3.85 (1H, dd, J=1.5, 7.5), 3.61 (1H, br s, OH), 3.51 (1H, dd, J=6.6, 8.3, H-2'), 3.42 (6H, s, 2×C$\underline{H}_3$O), 2.08 (3H, s, C$\underline{H}_3$CO), 1.81-1.25 (30H, unresolved, cyclohexyl).
$^{13}$C NMR ($CDCl_3$, 75 MHz) δ: 170.82 (CO), 110.9, 110.6, 108.9 (3×($CH_3)_2\underline{C}$), 105.3, 103.7 (C-1, C-1'), 78.5, 77.6, 77.6, 76.3, 74.7, 74.6, 72.8, 71.5 (C-2, C-3, C-4, C-5, C-2', C-3', C-4', C-5'), 64.3, 63.6 (C-6, C-6'), 56.1, 53.3 (2×$OCH_3$), 37.7-33.9, 25.1-23.6 (cyclohexyl).

Example 3

4-O-(6-O-trityl-3,4-O-isopropylidene-β-D-galactopyranosyl)-2,3:5,6-di-O-isopropylidene-D-glucose dimethyl acetal 3',4':2,3:5,6-Tri-O-isopropylidene-lactose dimethyl acetal (5.52 g, 10.9 mmol) is dissolved in dry pyridine (100 ml).

Trityl chloride (6.0 g, 21.5 mmol) is added together with DMAP (0.30 g) and the mixture is heated to 65° C. for 4 h. The mixture is evaporated in vacuo, coevaporated with toluene (3×30 ml). The residue is dissolved in EtOAc (50 ml), washed with $H_2O$ (50 ml), dried ($Na_2SO_4$), filtered and evaporated in vacuo. Purification by flash chromatography (hexane/EtOAc, 8:2, then 4:6) gives the product as an oil (3.0 g, 37%).

$^1$H NMR (CDCl$_3$, 500 MHz) δ: 7.45-7.22 (15H, 3×Ph), 4.38 (1H, d, J=8.5, H-1'), 4.38 (1H, m), 4.36 (1H, dd, J=6.5, 7.7), 4.27 (1H, d, J=6.1, H-1), 4.26 (1H, m), 4.14 (1H, dd, J=6.4, 8.8), 4.08 (1H, dd, J=5.6, 7.1), 4.00-3.97 (2H, unresolved), 3.85 (1H, dd, J=1.0, 7.6), 3.817 (1H, ddd, J=1.8, 5.3, 7.7), 3.56-3.52 (2H, unresolved), 3.25 (1H, dd, J=5.3, 8.5), 3.22 (3H, s, CH$_3$O), 3.09 (3H, s, CH$_3$O), 1.52, 1.50, 1.42, 1.34, 1.33, 1.32 (6×C(CH$_3$)$_2$).

$^{13}$C NMR (CDCl$_3$, 75 MHz) δ: 143.8, 128.6, 127.7, 127.0 (Ph), 110.1, 109.8, 108.2 (3×(CH$_3$)$_2$C), 104.5, 103.9 (C-1, C-1'), 86.7 (C(Ph)$_3$), 78.9, 77.9, 77.8, 76.1, 74.3, 74.2, 73.3, 72.5 (C-2, C-3, C-4, C-5, C-2', C-3', C-4', C-5'), 64.5, 62.0 (C-6, C-6'), 55.7, 52.2 (2×OMe), 28.2, 27.1, 26.3, 26.3, 25.5, 24.2 (6×C(CH$_3$)$_2$).

Example 4

4-O-(6-O-pivaloyl-3,4-O-isopropylidene-β-D-galactopyranosyl)-2,3:5,6-di-O-isopropylidene-D-glucose dimethyl acetal 3',4':2,3:5,6-Tri-O-isopropylidene-lactose dimethyl acetal (10 g, 19.7 mmol) was dissolved in DCM (80 ml) and pyridine (8 ml, 98.9 mmol) and cooled to 0° C. Pivaloyl chloride (8 ml, 39 mmol) was added dropwise and the mixture was stirred for 20 hours at room temperature. DCM (50 ml) was added and the mixture was washed with $H_2O$ (80 ml), aq. HCl (1M, 80 ml), $H_2O$ (80 ml), sat. NaHCO$_3$ (80 ml), dried (Na$_2$SO$_4$), filtered, evaporated and coevaporated with toluene. The residue was purified by flash chromatography (Hexane/EtOAc, 3:2) to give the product as a white foam (7.1 g, 61%).

$^1$H NMR (CDCl$_3$, 300 MHz) δ: 4.435 (1H, d, J=8.2, H-1'), 4.411 (1H, dd, J=6.0, 7.3, H-2), 4.361 (1H, d, J=6.03, H-1), 4.312 (1H, dd, J=6.8, 11.2, H-6'), 4.277 (1H, m), 4.243 (1H, dd, J=6.3, 11.1, H-6'), 4.173-4.034 (4H, unresolved), 3.997 (1H, dd, J=6.8, 8.8, H-6), 3.950 (1H, ddd, J=2.2, 6.3, 6.4), 3.905 (1H, dd, J=1.6, 7.3), 3.547 (1H, dd, J=7.1, 8.1, H-2'), 3.428, 3.416 (6H, 2×OMe), 1.500, 1.479, 1.374, 1.366, 1.318, 1.313 (6×3H, s, 6×C(CH$_3$)$_2$), 1.200 (9H, s, C(CH$_3$)$_3$).

$^{13}$C NMR (CDCl$_3$, 75 MHz) δ: 178.02 (CO), 110.11, 110.07, 108.19 (3×C(CH$_3$)$_2$), 104.99 (C-1), 103.44 (C-1'), 78.76, 77.79, 77.69, 75.93, 74.93, 74.07 (C-2'), 72.99, 64.53 (C-6'), 62.69 (C-6), 56.20, 53.05 (2×OCH$_3$), 38.62 (C(CH$_3$)$_3$), 28.02, 27.13, 27.01 (C(CH$_3$)$_3$), 26.34, 26.11, 25.55, 24.347 (6×CH$_3$).

Example 5

Compounds of general formula 6 were synthesized according to example 4 using the appropriate acylating agent.

a) 4-O-(6-O-(4-nitrobenzoyl)-3,4-O-isopropylidene-β-D-galactopyranosyl)-2,3:5,6-di-O-isopropylidene-D-glucose dimethyl acetal Yield: 98%, oil
$^1$H NMR (CDCl$_3$, 300 MHz): δ=8.30-8.23 (m, 4H), 4.65 (dd, 1H, J=4.5, 11.8), 4.58 (dd, 1H, J=7.3, 11.8), 4.44 (d, 1H, J=8.3), 4.42 (dd, 1H, J=6.2, 7.8), 4.27 (d, 1H, J=6.1), 4.27 (ddd, 1H, J=6.7, 6.7, 2.3), 4.18 (dd, 1H, J=5.5, 2.2), 4.16-4.10 (4H), 4.01 (dd, 1H, J=6.7, 8.8), 3.87 (dd, 1H, J=1.5, 7.8), 3.79 (s, 1H), 3.60 (dd, 1H, J=7.8, 7.8), 3.36, 3.35 (s, 2×3H), 1.52, 1.49, 1.36, 1.35, 1.34, 1.33 (s, 6×3H).

$^{13}$C NMR (CDCl$_3$, 75 MHz): δ=164.5, 150.6, 135.1, 131.0, 123.5, 110.5, 110.1, 108.3, 105.8, 103.9, 78.9, 77.8, 77.8, 76.6, 75.6, 74.2, 73.3, 71.4, 64.8, 64.7, 56.6, 54.3, 28.1, 27.2, 26.4, 26.3, 25.6, 24.7.

b) 4-O-(6-O-(4-phenylbenzoyl)-3,4-O-isopropylidene-β-D-galactopyranosyl)-2,3:5,6-di-O-isopropylidene-D-glucose dimethyl acetal Yield: 48%, colourless oil
$^1$H NMR (CDCl$_3$, 300 MHz) δ: 8.14-7.15 (9H, aromatic) 4.64 (1H, dd, J=4.9, 11.6, H-6a'), 4.55 (1H, dd, J=7.1, 11.6, H-6b'), 4.48 (1H, dd, J=5.9, 7.8, H-2), 4.48 (1H, d, J=8.1, H-1'), 4.27 (1H, d, J=6.1, H-1), 4.27 (1H, m), 4.22 (1H, dd, J=5.5, 2.3), 4.19-4.10 (4H, unresolved), 4.02 (1H, dd, J=6.8, 8.8, H-6b), 3.91 (1H, dd, J=1.5, 7.7, H-3), 3.63 (1H, s, OH), 3.61 (1H, dd, J=7.0, 6.9, H-2'), 3.35, 3.34 (2×3H, s, OCH$_3$), 1.54, 1.50, 1.40, 1.37, 1.36, 1.33 (6×3H, s, 6×C(CH$_3$)$_2$).

$^{13}$C NMR (CDCl$_3$, 75 MHz) δ: 166.2 (CO), 145.9, 139.8, 130.3-125.2 (aromatic C), 110.4, 110.1, 108.3 (3×C(CH$_3$)$_2$), 105.0, 103.7 (C-1, C-1'), 78.9, 77.8, 77.8, 76.4, 75.0, 74.2, 73.4, 71.6 (C-2, C-3, C-4, C-5, C-2', C-3', C-4', C-5'), 64.6, 64.0 (C-6, C-6'), 56.3, 53.2 (2×OCH$_3$), 28.1, 27.2, 26.4, 26.3, 25.6, 24.5 (6×CH$_3$).

c) 4-O-(6-O-propionyl-3,4-O-isopropylidene-β-D-galactopyranosyl)-2,3:5,6-di-O-isopropylidene-D-glucose dimethyl acetal Yield: 81%, colourless oil
$^1$H NMR (CDCl$_3$, 300 MHz): δ=4.42 (dd, 1H, J=6.2, 7.5), 4.40 (d, 1H, J=8.2), 4.35 (d, 1H, J=6.1), 4.32-4.24 (3H), 4.16-4.03 (4H), 3.99 (dd, 1H, J=6.8, 8.8), 3.93 (ddd, 1H, J=2.1, 5.2, 7.2), 3.88 (dd, 1H, J=1.6, 7.5, H-3), 3.54 (dd, 1H, J=8.0, 8.0, H-2'), 3.41, 3.41 (s, 2×3H), 2.34 (q, 2H), 1.49, 1.47, 1.37, 1.36, 1.31, 1.31 (s, 6×3H), 1.13 (t, 3H).

$^{13}$C NMR (CDCl$_3$, 75 MHz): δ=174.1, 110.3, 110.2, 108.3, 105.0, 103.6, 78.9, 77.9, 77.8, 76.3, 74.9, 74.1, 73.2, 71.4, 64.6, 63.2, 56.1, 53.0, 28.0, 27.3, 27.2, 26.3, 26.2, 25.6, 24.4, 8.95.

d) 4-O-(6-O-(4-chlorobenzoyl)-3,4-O-isopropylidene-β-D-galactopyranosyl)-2,3:5,6-di-O-isopropylidene-D-glucose dimethyl acetal White Foam
$^1$H NMR (CDCl$_3$): δ=8.10 and 7.42 (2 m, each 2H), 4.55 (2 ABq, each 1H, J=4.6, 7.4, 11.7), 4.45 (d, 1H, J=8.3), 4.43 (m, 1H), 4.27 (d, 1H, J=5.9), 4.11 (m, 2H), 3.37 and 3.34 (2 s, each 3H), 1.52, 1.48, 1.38, 1.36, 1.36 and 1.34 (6 s, each 3H).

$^{13}$C NMR (CDCl$_3$): δ=165.4, 139.6, 131.2, 128.7, 128.2, 110.4, 110.1, 108.3, 105.2, 103.8, 78.9, 77.8, 77.8, 76.5, 75.2, 74.2, 73.3, 71.5, 64.6, 64.2, 56.4, 53.5, 28.07, 27.2, 26.3, 26.2, 25.6, 24.6.

e) 4-O-(6-O-(4-phenylcarbamoyl-benzoyl)-3,4-O-isopropylidene-β-D-galactopyranosyl)-2,3:5,6-di-O-isopropylidene-D-glucose dimethyl acetal $^1$H-NMR (300 MHz, CDCl$_3$): δ=1.33 (s, 3H), 1.35 (s, 3H), 1.37 (s, 3H), 1.38 (s, 3H), 1.50 (s, 3H), 1.53 (s, 3H), 3.33 (s, 3H), 3.35 (s, 3H), 3.58-3.64 (m, 1H), 3.70 (d, 1H, J=1.1), 3.89 (dd, 1H, J=7.7, 1.4), 4.02 (dd, 1H, J=8.8, 6.8), 4.10-4.15 (m, 3H), 4.18-4.22 (m, 1H), 4.26-4.30 (m, 2H), 4.43-4.48 (m, 2H), 4.54-4.67 (m, 2H), 7.17 (t, 1H, J=7.4), 7.39 (t, 2H, J=7.6), 7.65 (d, 2H, J=7.6), 7.94 (d, 3H, J=8.5), 8.17 (d, 2H, J=8.4).

f) 4-O-(6-O-(4-(4-bromophenylcarbamoyl)-benzoyl)-3,4-O-isopropylidene-β-D-galactopyranosyl)-2,3:5,6-di-O-isopropylidene-D-glucose dimethyl acetal $^1$H-NMR (300 MHz, CDCl$_3$): δ=1.33 (s, 3H), 1.34 (s, 3H), 1.36 (s, 3H), 1.37 (s, 3H), 1.49 (s, 3H), 1.53 (s, 3H), 3.32 (s, 3H), 3.35 (s, 3H), 3.5 (d, 1H, J=4.5), 3.6 (t, 1H, J=7.9), 3.86-3.89 (m, 1H), 3.98-4.04 (m, 1H), 4.08-4.13 (m, 3H), 4.18-4.21 (m, 1H), 4.27-4.30 (m, 2H), 4.39-4.47 (m, 2H), 4.57-4.64 (m, 2H), 7.48 (d, 2H, J=8.8), 7.56 (d, 2H, J=8.8), 7.91 (d, 2H, J=8.3), 8.01 (s, 1H), 8.15 (d, 2H, J=8.3).

g) 4-O-(6-O-(4-benzamidobenzoyl)-3,4-O-isopropylidene-β-D-galactopyranosyl)-2,3:5,6-di-O-isopropylidene-D-glucose dimethyl acetal $^1$H-NMR (300 MHz, CDCl$_3$): δ=1.33 (s, 3H), 1.35 (s, 3H), 1.37 (s, 3H), 1.39 (s, 3H), 1.50 (s, 3H), 1.53 (s, 3H), 3.33 (s, 3H), 3.37 (s, 3H), 3.60 (t, 1H, J=7.8), 3.89 (dd, 1H, J=7.7, 1.4), 4.01 (dd, 1H, J=8.7, 6.8), 4.09-4.22 (m, 5H), 4.26-4.32 (m, 2H), 4.46-4.64 (m, 4H), 7.50-7.58 (m, 3H), 7.76 (d, 2H, J=8.7), 7.88 (d, 2H, J=7.9), 8.05 (s, 1H), 8.08 (d, 2H, J=8.7).
$^{13}$C-NMR (75 MHz, CDCl$_3$): δ=24.52, 25.63, 26.27, 26.38, 27.21, 28.11, 53.10, 56.34, 63.89, 64.64, 71.59, 73.37, 74.26, 74.99, 76.35, 77.85, 78.93, 103.73, 104.98, 108.27, 110.16, 110.38, 119.14, 125.37, 127.04, 128.90, 131.09, 132.26, 134.42, 142.36, 165.77.

h) 4-O-(6-O-(4-(4-nitrobenzamido)-benzoyl)-3,4-O-isopropylidene-β-D-galactopyranosyl)-2,3:5,6-di-O-isopropylidene-D-glucose dimethyl acetal $^1$H-NMR (300 MHz, CDCl$_3$): δ=1.33 (s, 3H), 1.34 (s, 3H), 1.37 (s, 3H), 1.38 (s, 3H), 1.49 (s, 3H), 1.51 (s, 3H), 3.33 (s, 3H), 3.37 (s, 3H), 3.60 (t, 1H, J=7.8 Hz), 3.89 (dd, 1H, J$^1$=7.7, 1.4 Hz), 4.01 (dd, 1H, J$^1$=8.7, 6.8 Hz), 4.08-4.26 (m, 5H), 4.26-4.37 (m, 2H), 4.40-4.63 (m, 4H), 7.77 (d, 2H, J=8.7 Hz), 8.04-8.09 (m, 4H), 8.31-8.34 (m, 3H).
$^{13}$C-NMR (75 MHz, CDCl$_3$): δ=24.47, 25.59, 26.23, 26.34, 27.18, 28.06, 53.09, 56.30, 63.98, 64.59, 71.51, 73.33, 74.27, 74.97, 76.35, 77.78, 77.87, 78.90, 103.67, 105.04, 108.26, 110.15, 110.38, 119.48, 123.98, 125.22, 126.01, 128.15, 128.39, 128.96, 131.08, 139.96, 141.72, 149.81, 163.82, 165.62.

i) 4-O-(6-O-(3,5-dinitrobenzoyl)-3,4-O-isopropylidene-β-D-galactopyranosyl)-2,3:5,6-di-O-isopropylidene-D-glucose dimethyl acetal Yield: 84%, pale yellow foam
$^{13}$C NMR (CDCl$_3$): 162.57, 148.92 (two carbons), 133.83, 129.80 (two carbons), 122.64, 110.88, 110.37, 108.53, 106.05, 104.19, 79.26, 78.01, 77.82, 77.14, 76.10, 74.38, 73.49, 71.36, 65.71, 64.89, 57.09, 54.77, 28.32, 27.26, 26.55, 26.50, 25.93, 24.84.

j) 4-O-(6-O-(naphthalen-2-ylacetyl)-3,4-O-isopropylidene-β-D-galactopyranosyl)-2,3:5,6-di-O-isopropylidene-D-glucose dimethyl acetal Yield: 89%, white foam
$^{13}$C NMR (CDCl$_3$): 171.48, 133.64, 132.70, 131.47, 128.52, 128.22, 127.88, 127.84, 127.45, 126.46, 126.13, 110.526, 110.50, 108.51, 105.53, 103.93, 79.14, 78.20, 78.07, 76.67, 75.47, 74.38, 73.30, 71.40, 64.84, 63.75, 56.47, 53.72, 41, 49, 28.30, 27.51, 26.64, 26.39, 25.88, 24.66.

Example 6

4-O-(6-O-(4-aminobenzoyl)-3,4-O-isopropylidene-β-D-galactopyranosyl)-2,3:5,6-di-O-isopropylidene-D-glucose dimethyl acetal Compound according to example 5a (400 mg, 608 μmol) is dissolved in 10 ml of THF and Pd/C (50 mg) is added. The suspension is stirred under H$_2$ atmosphere for three days until all starting material was consumed (TLC system: toluene-acetone 4:1 and 10% MeOH-DCM). The catalyst is filtrated over celite, and the residue is isolated by chromatography (5:1 toluene-acetone) as a white foam in 89% yield (341 mg).
$^{13}$C NMR (CDCl$_3$): 166.56, 151.12, 132.04 (two carbons), 119.51, 114.11 (two carbons), 110.55, 110.35, 108.51, 104.98, 103.98, 79.19, 78.07, 78.04, 76.55, 75.12, 74.53, 73.66, 71.94, 64.91, 63.59, 56.47, 53.12, 28.36, 27.44, 26.63, 26.51, 25.90, 24.75.

Example 7

Tetra-O-acetyl-L-fucose

Pyridine (295 ml, 3.65 mol) is cooled to 0° C. and L-Fucose (100 g, 609 mmol) is added during stirring. Ac$_2$O (287 ml, 3.04 mol) is added dropwise within 3 h. The reaction mixture is stirred for 2 h at 0° C. and for 24 h at room temperature. Methanol (25 ml, 618 mmol) is added dropwise and the reaction mixture is stirred for 30 min. The reaction mixture is then diluted with toluene (400 ml) and washed with water (3×300 ml). The aqueous phases are combined and extracted with toluene (300 ml). The organic phases are combined and washed with 1N HCl (3×500 ml), water (2×500 ml) and sat. NaHCO$_3$ solution (300 ml). The organic phase is dried and concentrated to dryness giving 197 g (98%) of product as a colourless syrup.

Example 8

Phenyl 2,3,4-tri-O-acetyl-1-thio-β-L-fucopyranoside

To a solution of compound of example 7 (196 g, 590 mmol) in toluene (200 ml) thiophenol (76 ml, 737 mmol) is added and the mixture is cooled to 0° C. BF$_3$.Et$_2$O (112 ml, 885 mmol) is added dropwise in 60 min., then the reaction mixture is stirred for 3 h at 0° C., 12 h at 5° C. and 2 h at room temperature. The obtained mixture is washed with water (500 ml), water/brine (1:1) mixture (700 ml), 1N NaOH/brine (1:1) mixture (400 ml), water/brine (1:1) mixture (700 ml) and brine (300 ml). The combined and dried organic phases are evaporated to dryness at 70° C. to give 224 g of the title compound (99%).

Example 9

Phenyl 1-thio-β-L-fucopyranoside

Compound of example 8 (224 g) is dissolved in methanol (500 ml) and NaOMe (2 g, 37 mmol) is added. The reaction mixture is stirred at 40° C. for 2$^1$/2 h. Methanol (250 ml) is distilled off and CO$_2$ is bubbled through the remaining solution for 5 min reaching pH=7. The reaction mixture is evaporated and isobutyl acetate (450 ml) is added. 50 ml of solvent is evaporated and the resulting mixture is subjected to crystallization by letting it at room temperature for 24 h. The white crystalline solid formed is filtered and washed with tert-butyl methyl ether (200 ml) giving 110 g (73%) of product after drying.

Example 10

Phenyl 3,4-O-isopropylidene-1-thio-β-L-fucopyranoside

Compound of example 9 (150 g, 0.58 mol) is suspended in 2,2-dimethoxypropane (550 ml, 4.5 mol) and a catalytic amount of p-TsOH (1.19 g, 6.2 mmol) is added. After stirring the mixture for 12 hours at room temperature $Et_3N$ (6 ml) is added slowly to neutralize the acid. The solution is evaporated to dryness (174 g), the residue is dissolved in diethyl ether (250 ml) and cooled to 0° C., then hexane (250 ml) is added dropwise to the mixture during vigorous stirring. The mixture is kept in fridge (5° C.) for 2 days and the precipitated white solid is filtrated and washed with hexane (200 ml) to give 145.48 g of compound (85%). the mother liquor is evaporated, the residue is dissolved in $Et_2O$ (25 ml) and hexane (25 ml) is added dropwise to it to crystallize 11, 51 g of second crop. Combined yield: 91.5%. M.p.: 81° C., $[α]_D$=−28.15 (1.03, MeOH).

Example 11

Phenyl 2-O-benzyl-3,4-O-isopropylidene-1-thio-β-L-fucopyranoside

Compound of example 10 (157 g, 0.53 mol) is added to dry DMF (800 ml) and cooled to 0° C. NaH (1,2 eq) is added carefully in portions to the cooled solution and the stirring is continued for ½ hour at the same temperature. Benzyl bromide (76.3 ml, 0.635 mol) is then added dropwise and the temperature is allowed to warm to room temperature. The reaction mixture is stirred for 1 hour then cooled to 0° C. and MeOH (60 ml) is added dropwise. The resulting mixture is evaporated, the residue is dissolved in $CH_2Cl_2$ (1500 ml) and washed with water (3×750 ml). The organic phase is dried ($Na_2SO_4$), filtrated and evaporated to yield 205.2 g of a brownish-yellow syrup (100%).

Example 12

Phenyl 2-O-benzyl-1-thio-β-L-fucopyranoside

To a solution of compound of example 11 (100.0 g, 0.26 mol) in MeOH (300 ml) 60% acetic acid (500 ml) is added. The mixture is stirred at 80° C. for four hours then evaporated. The remaining solvents are co-evaporated with the aid of toluene (100 ml). The residue is dissolved in MeOH (200 ml) under heating and the solution is allowed to cool to room temperature. White crystals precipitate which are filtrated, washed with cold methanol and dried. Yield: 50.52 g (56.1%). A first (15.81 g, 17.5%) and a second crop (10.42 g, 11.6%) of product can be crystallized from the mother liquor. M.p.: 105-107° C., $[α]_D$=−16.93 (1.00, $CHCl_3$).

Example 13

Phenyl 3,4-di-O-benzoyl-2-O-benzyl-1-thio-β-L-fucopyranoside

Compound of example 12 (10 g, 29 mmol) is dissolved in the mixture of pyridine (12 ml, 145 mmol) and DCM (35 ml). The solution is cooled to 0° C. and benzoyl-chloride (10 ml, 87 mmol) is added dropwise when the mixture becomes a thick suspension. It is stirred at room temperature for 3.5 hours then evaporated, the residue is dissolved in toluene (50 ml), the solution is washed with water (2×30 ml), 1 N HCl solution (20 ml), water (30 ml), sat. $NaHCO_3$ solution (30 ml) and water:brine=1:1 (40 ml). The organic phase is dried, evaporated and the yellow syrup obtained is crystallized from MeOH (50 ml). White crystals precipitate which are filtrated, washed with cold MeOH (25 ml) and dried. Yield: 14.63 g (91%). M.p.: 98-100° C., $[α]_D$=−112 (1.02, $CHCl_3$).

$^1$H NMR ($CDCl_3$, 300 MHz): δ=7.98-7.17 (m, 20H), 5.67-5.65 (m, 1H), 5.45 (dd, 1H, J=3.3 Hz, J=9.6 Hz), 4.84-4.76 (m, 2H), 4.57 (d, 1H, J=10.5), 4.07-3.90 (m, 2H), 2.15 (s, 3H), 2.25 (d, 3H, J=6.3 Hz).

$^{13}$C NMR ($CDCl_3$, 75 MHz): δ=166.1, 165.7, 137.9-128.1, 87.2, 75.6, 75.6, 75.1, 73.7, 72.0, 17.1.

Example 14

Phenyl 3,4-di-O-acetyl-2-O-benzyl-1-thio-β-L-fucopyranoside

The title compound is obtained by the method according to example 13 using acetic anhydride as acylating agent. White crystals, yield: 88%, m.p.: 124° C. (EtOH), $[α]_D$=−14.9 (1.00, $CHCl_3$).

$^1$H NMR ($CDCl_3$): 7.61-7.58 (m, 2H), 7.34-7.26 (m, 8H), 5.25 (dd, 1H), 5.02 (dd, 1H), 4.84 and 4.57 (AB-system), 4.71 (d, 1H), 3.79 (qd, 1H), 3.72 (t, 1H), 2.15 (s, 3H), 1.93 (s, 3H), 1.22 (d, 3H).

Example 15

Phenyl 2-O-benzyl-3,4-di-O-(4-chlorobenzoyl)-1-thio-β-L-fucopyranoside

The title compound is obtained by the method according to example 13 using 4-chlorobenzoyl chloride as acylating agent. M.p.: 142-144.5° C.

$^1$H NMR (600 MHz, $CDCl_3$) δ: 1.30 d 3H, 3.87 t 1H, 4.01 dq 1H, 4.54 and 4.81 ABq 2H, 4.78 d 1H, 5.28 dd 1H, 5.58 dd 1H, 7.15 m 5H, 7.25 m 2H, 7.37 m 3H, 7.43 m 2H, 7.65 m 2H, 7.69 m 2H, 7.84 m 2H.

$^{13}$C NMR (150 MHz, $CDCl_3$) δ: 16.7, 71.9, 73.3, 74.8, 75.3, 75.4, 87.0, 127.8, 127.9, 128.0, 128.3, 128.7, 128.9, 129.0, 130.9, 131.2, 133.0, 164.5, 164.9.

Example 16

Phenyl 2-O-(4-methylbenzyl)-3,4-O-isopropylidene-1-thio-β-L-fucopyranoside

4-Methylbenzyl chloride (60 g, 430 mmol, 1.1 eq), 25% NaOH solution (120 ml) and TBAHS (4.0 g, 11.7 mmol, 0.03 eq) are added to compound of example 10. The mixture is stirred at 90° C. for 3 hours. After completion of the reaction MeOH (1.6 ml, 39.0 mmol, 0.1 eq) is added, the mixture is stirred for 30 min and the solvents are removed at 50° C. The residue is used for the next step without further purification. A small sample is purified for characterization.

$^1$H NMR ($CDCl_3$, 300 MHz): δ=7.55-7.52 (m, 4H), 7.32-7.26 (m, 5H), 7.14 (d, 2H, J=8.2 Hz), 4.64-4.57 (m, 2H), 4.22 (t, 1H, J=5.9 Hz, J=5.9 Hz), 4.04 (dd, 1H, J=2.1 Hz, J=5.6 Hz), 3.86-3.79 (m, 1H), 3.52-3.47 (m, 1H), 2.34 (s, 3H), 1.42-1.36 (m, 9H).

$^{13}$C NMR (CDCl$_3$, 75 MHz): δ=137.6, 135.1, 134.1, 132.3, 129.2, 129.0, 128.6, 127.6, 109.9, 86.3, 80.1, 78.1, 76.6, 73.6, 72.6, 28.2, 26.7, 21.5, 17.7.

Example 17

Phenyl 2-O-(4-methylbenzyl)-1-thio-β-L-fucopyranoside

To the crude material obtained in example 16 isopropanol (100 ml) and water (15 ml) are added and the pH is adjusted by addition of 4N HCl solution (4 ml, pH=3). Then IR 120 resin (15 g) is added and the mixture is stirred under reflux for 1 hour. After completion of the reaction the reaction mixture is filtered at 70° C. and a mixture of water-MeOH-hexane-isopropanol (150 ml/400 ml/150 ml/1.7 l) is added. The compound is subjected to crystallization by adding seeding crystals and allowed to stand at 5-10° C. for several hours. The white crystalline solid is filtered off and washed with 200 ml of hexane giving 87.7 g (62%) of pure crystalline compound. After mother liquor treatment 34.2 g of compound is also obtained. Overall yield: 121.9 g (86%). Mp: 146-147° C.

$^1$H NMR (CDCl$_3$, 300 MHz): δ=7.56-7.52 (m, 2H), 7.3-7.24 (m, 5H), 7.13 (d, 2H, J=7.9 Hz), 4.87 (d, 1H, J=10.8 Hz), 4.63-4.55 (m, 2H), 3.66-3.49 (m, 4H), 2.31 (s, 3H), 1.30 (d, 3H, J=6.5 Hz).

$^{13}$C NMR (CDCl$_3$, 75 MHz): δ=138.1, 135.3, 134.4, 131.8, 129.5, 129.2, 128.7, 127.6, 87.7, 78.1, 75.4, 75.4, 74.7, 71.9, 21.5.

Example 18

Phenyl 3,4-di-O-benzoyl-2-O-(4-methylbenzyl)-1-thio-β-L-fucopyranoside

Pyridine (33.6 ml, 416 mmol, 3 eq) is added to a mixture of compound according to example 17 (50 g, 138.7 mmol) in DCM (70 ml) at 0-5° C. Then benzoylchloride (35.4 ml, 305 mmol, 2.2 eq) is slowly added (the temperature cannot reach more than 15° C.) to the mixture during 1 hour. After the addition the reaction mixture is stirred for 2 hours at rt. Then at 0-5° C. MeOH (3 ml, 0.3 eq) is slowly added and the reaction mixture is stirred for 30 min at rt. Again at 0° C. 4M HCl solution (32 ml) is slowly added and the reaction mixture is stirred for 30 min at rt. The organic phase is extracted, washed 2 times with water (2×30 ml), dried, evaporated at 60° C. and MeOH (200 ml) is added. The mixture is then partially evaporated at 60° C. and the compound starts to crystallize: 77.1 g (98%). Mp: 81-83° C.

$^1$H NMR (CDCl$_3$, 300 MHz): δ=7.91-7.19 (m, 15H), 6.98 (d, 2H, J=7.9 Hz), 6.86 (d, 2H, 7.9 Hz), 5.57-5.56 (m, 1H), 5.35 (dd, 1H, J=3.3 Hz, J=9.6 Hz), 4.75-4.66 (m, 2H), 4.46 (d, 1H, J=10.4), 3.99-3.84 (m, 2H), 2.15 (s, 3H), 2.25 (d, 3H, J=6.4 Hz).

$^{13}$C NMR (CDCl$_3$, 75 MHz): δ=166.0, 165.7, 137.7, 134.8, 133.6, 133.3, 133.2, 133.2, 133.1, 130.2, 129.9, 129.8, 129.8, 129.3, 129.2, 128.8, 128.5, 128.0, 87.3, 75.5, 75.4, 74.9, 73.7, 72.0, 21.4, 17.0.

Example 19

Phenyl 3,4-di-O-(4-chlorobenzoyl)-2-O-(4-methyl-benzyl)-1-thio-β-L-fucopyranoside Starting from compound of example 17 (30 g) and using 4-chlorobenzoyl chloride (26.7 ml) the title compound is obtained according to the methodology described in example 18: 50.3 g of yellow syrup.

$^1$H NMR (CDCl$_3$, 300 MHz): δ=7.92-7.15 (17H), 5.50 (m, 1H), 5.30 (dd, 1H, J=3.3, 9.6), 4.71 (d, 1H, J=9.6), 4.44 (d, 1H, J=10.8), 3.94 (m, 1H, J=0.6, 6), 3.80 (t, 1H, 9.6), 2.15 (s, 3H), 1.23 (d, 1H, J=6.3).

$^{13}$C NMR (CDCl$_3$, 75 MHz): δ=165.2, 164.7, 140.2, 139.8, 137.8, 134.7, 133.2-128.0, 87.1, 75.6, 75.4, 74.8, 73.4, 72.2, 21.4, 17.0.

Example 20

Typical Glycosylation Procedure Leading to Compounds of General Formula 4

To a 0-10° C. cooled solution of the donor (1.1-1.2 eq) and the acceptor (1.0 eq) in DCM-THF 5:1-9:1 (2.5-4 volumes) NBS (1.1-1.2 eq) is added followed by triflic acid (0.01-0.025 eq). The reaction mixture stirred for 15 min. 25% Ammonium hydroxide solution (2 eq) is then added to quench the reaction. The organic phase is separated and concentrated, and the residue is purified by crystallization, column chromatography or used further as crude. Yields range between 50-87%.

a) O-(2-O-benzyl-3,4-di-O-(4-chlorobenzoyl)-α-L-fucopyranosyl)-(1→2)-O-(6-O-(4-chlorobenzoyl)-3,4-isopropylidene-β-D-galactopyranosyl)-(1→4)-2,3:5,6-di-O-isopropylidene-D-glucose dimethyl acetal donor: compound of example 15, acceptor: compound of example 5d White crystals, mp: 109.4-111.7° C.

$^1$H NMR (CDCl$_3$) δ: 1.15 (d, 3H, J=5.7 Hz); 1.4 (m, 12H); 1.55 (m, 6H); 3.35 (s, 3H); 3.38 (s, 3H); 3.8 (t, 1H, J=6 Hz); 3.95-4.4 (m, 10H); 4.5-4.8 (m, 7H); 5.55 (m, 1H); 4.63-4.71 (m, 2H); 7.25 (m, 7H); 7.4 (m, 4H); 7.7 (d, 2H, J=8.6); 7.85 (d, 2H, J=8.6); 8.00 (d, 2H, J=9.5).

$^{13}$C NMR (CDCl$_3$) δ: 16.02, 24.62, 26.29, 26.68, 26.72, 27.16, 27.84, 52.64, 56.07, 63.81, 64.59, 64.85, 70.29, 70.71, 72.03, 72.61, 72.78, 73.64, 74.74, 74.84, 76.66, 76.87, 77.32, 79.96, 95.24, 100.84, 105.26, 108.74, 109.84, 110.33, 127.59, 127.78, 127.9, 128.11, 128.16, 128.21, 128.39, 128.62, 128.68, 130.77, 130.96, 137.66, 139.13, 139.46, 139.56, 164.17, 164.90, 165.24.

b) O-(2-O-benzyl-3,4-di-O-benzoyl-α-L-fucopyranosyl)-(1→2)-O-(6-O-(4-chlorobenzoyl)-3,4-isopropylidene-β-D-galactopyranosyl)-(1→4)-2,3:5,6-di-O-isopropylidene-D-glucose dimethyl acetal donor: compound of example 13, acceptor: compound of example 5d White Foam $^1$H-NMR (300 MHz, CDCl$_3$): δ=1.18 (d, 3H, J=6.5 Hz), 1.37 (s, 3H), 1.39 (s, 3H), 1.41 (s, 3H), 1.44 (s, 3H), 1.56 (s, 6H), 3.35 (s, 3H), 3.39 (s, 3H), 3.81 (dd, 1H, J=6.6 Hz, J=7.6 Hz), 3.97 (d, 1H, J=4.9 Hz), 4.07-4.14 (m, 3H), 4.20-4.25 (m, 3H), 4.31 (d, 1H, J=6.2 Hz), 4.37 (d, 2H, J=6.2 Hz), 4.54-4.60 (m, 4H), 4.69 (d, 2H, J=10.4 Hz), 4.76 (d, 1H, J=7.9 Hz), 5.64 (d, 1H, J=3.4 Hz), 5.68-5.73 (m, 2H), 7.21-7.31 (m, 8H), 7.41-7.48 (m, 5H), 7.81 (d, 2H, J=7.1 Hz), 7.96 (d, 2H, 8.1 Hz), 8.01 (d, 2H, J=8.6 Hz).

$^{13}$C-NMR (75 MHz, CDCl$_3$): δ=165.88, 165.38, 165.20, 139.58, 137.90, 133.06, 132.73, 131.06, 129.90, 129.75, 129.71, 129.56, 128.73, 128.34, 128.18, 128.10, 127.85, 127.59, 110.41, 109.97, 108.87, 105.39, 101.02, 95.56, 79.99, 76.87, 76.74, 74.96, 74.84, 73.68, 73.12, 72.48, 72.32, 70.78, 70.23, 65.02, 64.88, 63.92, 56.16, 52.66, 27.92, 27.29, 26.84, 26.80, 26.38, 24.78, 16.14.

c) O-(2-O-benzyl-3,4-di-O-benzoyl-α-L-fucopyranosyl)-(1→2)-O-(6-O-pivaloyl-3,4-isopropylidene-β-D-galactopyranosyl)-(1→4)-2,3:5,6-di-O-isopropylidene-D-glucose dimethyl acetal donor: compound of example 13, acceptor: compound of example 4
White Foam
$^1$H-NMR (300 MHz, CDCl$_3$): δ=1.17 (d, 3H, J=6.5 Hz), 1.22 (s, 9H), 1.36 (s, 3H), 1.39 (s, 3H), 1.41 (s, 3H), 1.42 (s, 3H), 1.54 (s, 6H), 3.44 (s, 6H), 3.77 (dd, 1H, J=6.6 Hz, J=8.0 Hz), 3.90-3.96 (m, 2H), 4.08-4.15 (m, 3H), 4.21-4.24 (m, 2H), 4.27-4.34 (m, 4H), 4.40 (d, 1H, J=6.3 Hz), 4.52-4.59 (m, 2H), 4.63-4.75 (m, 3H), 5.62 (d, 1H, J=3.3 Hz), 5.67-5.71 (m, 2H), 7.20-7.31 (m, 8H), 7.40-7.47 (m, 3H), 7.78-7.83 (m, 2H), 7.93-7.97 (m, 2H).
$^{13}$C-NMR (75 MHz, CDCl$_3$): δ=177.92, 165.85, 165.17, 137.89, 133.04, 132.70, 129.88, 129.73, 129.68, 129.54, 128.32, 128.15, 128.07, 127.82, 127.55, 110.18, 109.86, 108.82, 105.15, 101.11, 95.45, 79.95, 76.85, 76.75, 74.78, 74.54, 73.31, 73.04, 72.46, 72.20, 70.40, 70.20, 64.97, 64.81, 62.27, 56.04, 52.43, 38.66, 27.92, 27.22, 27.03, 26.82, 26.75, 26.29, 24.82, 16.11.

d) O-(2-O-(4-methylbenzyl)-3,4-di-O-benzoyl-α-L-fucopyranosyl)-(1→2)-O-(6-O-pivaloyl-3,4-isopropylidene-β-D-galactopyranosyl)-(1→4)-2,3:5,6-di-O-isopropylidene-D-glucose dimethyl acetal donor: compound of example 18, acceptor: compound of example 4
White Foam
$^1$H NMR (CDCl$_3$, 300 MHz): δ=7.95 (d, 2H, J=7.2 Hz), 7.79 (d, 2H, J=7.2 Hz), 7.59-7.23 (m, 6H), 7.15 (d, 2H, J=7.9 Hz), 7.00 (d, 2H, 7.8), 5.70-5.63 (m, 3H), 4.72-3.89 (m, 17H), 3.70 (t, 1H, J=7.2 Hz), 3.44 (s, 6H), 2.27 (s, 3H), 1.54-1.16 (m, 30H).
$^{13}$C NMR (CDCl$_3$, 75 MHz): δ=178.2, 166.13, 165.5, 137.5, 135.1, 133.4, 133.0, 130.2, 130.0, 130.0, 129.9, 129.8, 129.1, 128.7, 128.6, 128.6, 128.5, 128.4, 128.3, 110.5, 110.1, 109.1, 105.5, 101.5, 95.8, 80.2, 75.1, 74.9, 73.6, 73.1, 72.8, 72.4, 70.7, 70.5, 65.3, 65.1, 62.6, 56.3, 52.8, 39.0, 28.2, 27.6, 27.3, 27.2, 27.1, 26.6, 25.1, 21.4, 16.4.

e) O-(2-O-(4-methylbenzyl)-3,4-di-O-(4-chlorobenzoyl)-α-L-fucopyranosyl)-(1→2)-O-(6-O-pivaloyl-3,4-isopropylidene-β-D-galactopyranosyl)-(1→4)-2,3:5,6-di-O-isopropylidene-D-glucose dimethyl acetal donor: compound of example 19, acceptor: compound of example 4
White Foam
$^1$H NMR (CDCl$_3$, 300 MHz): δ=7.97-7.00 (m, 12H), 5.68-5.58 (m, 3H), 4.73-3.75 (m, 18H), 3.45 (s, 6H), 2.29 (s, 3H), 1.55-1.16 (m, 30H).
$^{13}$C NMR (CDCl$_3$, 75 MHz): δ=178.2, 165.3, 164.5, 139.9-127.4, 110.5, 110.2, 109.1, 105.5, 101.4, 95.6, 80.3, 75.0, 75.0, 73.7, 73.0, 72.9, 72.3, 70.7, 65.0, 62.6, 56.4, 52.8, 52.5, 39.0, 28.2, 27.5, 27.4, 27.1, 26.6, 25.1, 21.4, 16.4.

f) O-(2-O-(4-methylbenzyl)-3,4-di-O-benzoyl-α-L-fucopyranosyl)-(1→2)-O-(6-O-(4-chlorobenzoyl)-3,4-isopropylidene-β-D-galactopyranosyl)-(1→4)-2,3:5,6-di-O-isopropylidene-D-glucose dimethyl acetal donor: compound of example 18, acceptor: compound of example 5d
White Foam
$^1$H NMR (CDCl$_3$, 300 MHz): δ=7.97-6.93 (m, 18H), 5.64-5.54 (m, 3H), 4.60-3.70 (m, 18H), 3.31 (s, 3H), 3.27 (s, 3H), 2.22 (s, 3H), 1.48-1.24 (m, 18H), 1.11 (d, 3H, J=6.3 Hz).
$^{13}$C NMR (CDCl$_3$, 75 MHz): δ=165.7, 165.6, 165.5, 139.8-128.0, 110.7, 110.3, 109.1, 105.7, 102.4, 95.9, 80.2, 77.9-70.5, 65.3, 65.1, 64.2, 56.4, 52.9, 28.2, 27.7, 27.3, 27.2, 26.4, 25.1, 21.3, 16.4.

g) O-(2-O-(4-methylbenzyl)-3,4-di-O-(4-chlorobenzoyl)-α-L-fucopyranosyl)-(1→2)-O-(6-O-(4-chlorobenzoyl)-3,4-isopropylidene-β-D-galactopyranosyl)-(1→4)-2,3:5,6-di-O-isopropylidene-D-glucose dimethyl acetal donor: compound of example 19, acceptor: compound of example 5d
White Foam
$^1$H NMR (CDCl$_3$, 300 MHz): δ=7.95-6.95 (m, 16H), 5.59-5.50 (m, 3H), 4.69-3.69 (m, 18H), 3.31 (s, 3H), 3.28 (s, 3H), 2.23 (s, 3H), 1.55-1.30 (m, 18H), 1.09 (d, 3H, J=6.6 Hz).
$^{13}$C NMR (CDCl$_3$, 75 MHz): δ=165.6, 165.3, 164.5, 139.9-128.2, 110.7, 110.2, 109.1, 105.7, 101.2, 95.7, 80.3, 77.7-70.6, 65.2, 65.0, 64.2, 56.4, 53.0, 29.2, 28.2, 27.7, 27.1, 26.6, 25.0, 21.4, 16.4.

h) O-(2-O-benzyl-3,4-di-O-benzoyl-α-L-fucopyranosyl)-(1→2)-O-(6-O-benzoyl-3,4-isopropylidene-β-D-galactopyranosyl)-(1→4)-2,3:5,6-di-O-isopropylidene-D-glucose dimethyl acetal donor: compound of example 13, acceptor: 4-O-(6-O-benzoyl-3,4-O-isopropylidene-β-D-galactopyranosyl)-2,3:5,6-di-O-isopropylidene-D-glucose dimethyl acetal [1]
Yellow Syrup
$^1$H-NMR (CDCl$_3$, 600 MHz): δ1.17 (3H, d, J=6.5 Hz), 1.36 (3H, s), 1.37 (3H, s), 1.38 (3H, s), 1.42 (3H, s), 1.53 (3H, s), 1.54 (3H, s), 3.33 (3H, s); 3.36 (3H, s), 3.80 (1H, dd, J=7.8, 6.5 Hz), 3.97 (1H, dd, J=5.8, 1.3 Hz), 4.06-4.13 (3H, m), 4.17-4.25 (3H, m), 4.30 (1H, dd, J=6.1, 6.0 Hz), 4.34-4.38 (2H, m), 4.52-4.60 (4H, m), 4.64 (1H, d, J=12.3 Hz), 4.71 (1H, d, J=12.3 Hz), 4.75 (1H, d J=8.0 Hz), 5.62 (1H, d J=3.9 Hz), 5.66 (1H, d, J=3.8 Hz); 5.69 (1H, dd, J=11.1, 3.8 Hz), 7.16-7.29 (7H, m), 7.38-7.48 (5H, m), 7.54-7.60 (2H, m), 7.79 (2H, m), 7.94 (2H, m), 8.05 (2H, m).

i) O-(2-O-benzyl-3,4-di-O-(4-chlorobenzoyl-α-L-fucopyranosyl)-(1→2)-O-(6-O-pivaloyl-3,4-isopropylidene-β-D-galactopyranosyl)-(1→4)-2,3:5,6-di-O-isopropylidene-D-glucose dimethyl acetal donor: compound of example 15, acceptor: compound of example 4
White Foam
$^1$H NMR (CDCl$_3$, 300 MHz): δ=7.88-7.13 (m, 13H), 5.70-5.58 (m, 3H), 4.75-3.75 (m, 18H), 3.45 (s, 6H), 2.29 (s, 3H), 1.55-1.16 (m, 30H).
$^{13}$C NMR (CDCl$_3$, 75 MHz): δ=178.2, 165.3, 164.5, 139.9-128.0, 110.5, 110.1, 109.1, 105.5, 101.4, 95.6, 74.0, 73.7, 73.1, 72.9, 72.3, 70.7, 65.2, 65.0, 62.6, 56.4, 52.8, 39.0, 28.2, 27.5, 27.3, 27.1, 26.6, 25.1, 16.4.

Example 21

Typical Procedure Converting Compounds of General Formula 4 to Compounds of General Formula 3

Method A: a suspension/solution of a compound of general formula 4 in a mixture MeCN—$H_2O$ 7:1 (4-8 volumes) in the presence of pTsOH monohydrate (0.2-0.25 eq) is heated to 45° C. and stirred for 7-24 hours. The acid is neutralized by triethyl amine, the solvents are evaporated and the residue is crystallized or purified by chromatography giving the compounds in 29-78% yield.

Method B: a compound of general formula 4 is dissolved in acetone (5-15 volumes) and cc.HCl-water 1:1 (1-3 volumes) is added to the solution. It is stirred at 40-60° C. for 3-6 hours. 25% Ammonium hydroxide solution is added to reach pH=9. The reaction mixture is diluted with water and ethyl acetate (each 5-15 volumes), extracted and the organic phase is evaporated to give the end product in 85-95% yield.

a) O-(2-O-(4-methylbenzyl)-3,4-di-O-benzoyl-α-L-fucopyranosyl)-(1→2)-O-(6-O-(4-chlorobenzoyl)-β-D-galactopyranosyl)-(1→4)-D-glucose From Compound of Example 20f, Method A, Colourless Solid $^1$H NMR (CDCl$_3$, 300 MHz): δ=7.95-6.74 (m, 18H), 5.67-5.21 (m, 4H), 4.74-3.07 (m, 17H), 2.16 (s, 3H), 1.09-1.06 (m, 3H).

$^{13}$C NMR (CDCl$_3$, 75 MHz): δ=166.1, 166.0, 165.8, 139.9-128.0, 101.8, 99.0, 92.4, 78.7-60.9, 21.7, 16.3.

b) O-(2-O-(4-methylbenzyl)-3,4-di-O-(4-chlorobenzoyl)-α-L-fucopyranosyl)-(1→2)-O-(6-O-(4-chlorobenzoyl)-β-D-galactopyranosyl)-(1→4)-D-glucose From Compound of Example 20g, Method A, White Crystals, Mp.: 235-237° C. (Toluene/Acetone).

$^1$H NMR (CDCl$_3$, 300 MHz): δ=7.92-6.73 (m, 16H), 5.60-5.18 (m, 4H), 4.81-3.08 (m, 17H), 2.18 (s, 3H), 1.14-1.02 (m, 3H).

$^{13}$C NMR (CDCl$_3$, 75 MHz): δ=165.8, 165.3, 164.8, 140.2-127.7, 101.8, 96.6, 92.5, 79.3-60.9, 21.4, 16.2.

c) O-(2-O-(4-methylbenzyl)-3,4-di-O-(4-chlorobenzoyl)-α-L-fucopyranosyl)-(1→2)-O-(6O-pivaloyl-β-D-galactopyranosyl)-(1→4)-D-glucose From Compound of Example 20e, Method A, Colourless Solid $^1$H NMR (CDCl$_3$, 300 MHz): δ=7.90-6.87 (m, 12H), 5.69-5.30 (m, 4H), 4.74-3.01 (m, 17H), 2.27 (s, 3H), 1.25-1.09 (m, 12H).

$^{13}$C NMR (CDCl$_3$, 75 MHz): δ=178.8, 165.3, 165.2, 140.2-127.9, 101.5, 98.5, 92.4, 78.5-58.9, 27.5, 21.4, 16.3.

d) O-(2-O-(4-methylbenzyl)-3,4-di-O-benzoyl-α-L-fucopyranosyl)-(1→2)-O-(6-O-pivaloyl-β-D-galactopyranosyl)-(1→4)-D-glucose From Compound of Example 20d, Method A, Colourless Solid $^1$H NMR (CDCl$_3$, 300 MHz): δ=7.95-6.98 (m, 14H), 5.86-5.13 (m, 4H), 4.72-3.00 (m, 17H), 2.26 (s, 3H), 1.24-1.07 (m, 12H).

$^{13}$C NMR (CDCl$_3$, 75 MHz): δ=178.8, 166.2, 166.0, 138.3-128.5, 101.6, 99.0, 92.3, 78.8-58.9, 27.3, 21.4, 16.3.

e) O-(2-O-benzyl-3,4-di-O-(4-chlorobenzoyl)-α-L-fucopyranosyl)-(1→2)-O-(6-O-(4-chlorobenzoyl)-β-D-galactopyranosyl)-(1→4)-D-glucose From Compound of Example 20A, Method A, White Crystals.

Mixture of α/β anomers: mp. 226-228° C.

$^1$H NMR (CDCl$_3$) δ=1.15 (d, 3H, J=6.5 Hz); 3.15-4.2 (m, 15H); 4.4-4.95 (m, 15H); 5.12 (d, 0.7H, J=3.9 Hz); 5.6 (m, 2H); 5.9 (d, 1H, 3.6 Hz); 7.25 (m, 7H); 7.45 (m, 4H); 7.65 (d, 2H, J=8.5 Hz); 7.85 (d, 2H, J=8.6 Hz); 8.1 (d, 2H, J=8.1 Hz).

$^{13}$C NMR (CDCl$_3$) δ=15.28, 18.49, 60.16, 61.23, 61.65, 66.72, 68.92, 69.27, 69.29, 70.46, 71.39, 71.46, 71.72, 71.76, 72.08, 73.97, 74.00, 74.03, 74.08, 74.45, 75.05, 75.22, 75.30, 75.39, 75.43, 75.88, 91.92, 96.02, 96.92, 96.95, 100.21, 100.25, 128.50, 128.80, 128.91, 137.26, 137.27, 138.82, 140.57, 140.70, 140.93, 166.07, 166.52, 166.86.

β-anomer: mp. 136-141° C.

$^1$H NMR (CDCl$_3$) δ=1.06 (d, 3H, J=6.6 Hz); 3.35 (m, 3H); 3.5 (m, 2H); 3.7 (m, 1H); 3.8-4.2 (m, 7H); 4.4-4.7 (m, 6H); 5.55 (m, 2H); 5.9 (d, 1H, J=3.4 Hz); 7.1-7.6 (m, 11H); 7.65 (d, 2H, J=8.5 Hz); 7.85 (d, 2H, J=8.6 Hz); 8.1 (d, 2H, J=8.1 Hz).

$^{13}$C NMR (CDCl$_3$) δ=16.30, 61.57, 65.18, 65.99, 66.02, 70.86, 71.70, 72.63, 73.83, 73.89, 74.23, 74.27, 75.83, 75.88, 75.96, 75.99, 76.19, 76.24, 76.66, 78.89, 97.95, 98.01, 102.24, 128.97, 129.30, 129.39, 129.46, 129.75, 129.82, 130.09, 132.08, 132.22, 132.48, 138.82, 140.57, 140.70, 140.93, 166.07, 166.52, 166.86.

f) O-(2-O-benzyl-3,4-di-O-benzoyl-α-L-fucopyranosyl)-(1→2)-O-(6-O-(4-chlorobenzoyl)-β-D-galactopyranosyl)-(1→4)-D-glucose From Compound of Example 20b, Method A, Colourless Solid $^1$H-NMR (300 MHz, CDCl$_3$/MeOH 9:1): δ=1.10 (d, 3H, J=6.5 Hz), 1.20 (d, 0.7H, J=6.6 Hz), 3.37-3.55 (m, 5H), 3.67-3.93 (m, 6H), 3.98-4.10 (m, 1H), 4.25-4.65 (m, 5H), 5.12 (d, 1H, J=3.7 Hz), 5.47-5.64 (m, 3H), 7.00-7.60 (m, 12H), 7.71 (d, 2H, J=7.4 Hz), 7.85 (d, 2H, J=8.3 Hz), 7.94-7.98 (m, 3H).

g) O-(2-O-benzyl-3,4-di-O-benzoyl-α-L-fucopyranosyl)-(1→2)-O-(6-O-benzoyl-β-D-galactopyranosyl)-(1→4)-D-glucose From compound of Example 20h, Method B, Light Yellow Syrup $^{13}$C-NMR (150 MHz, DMSO-d$_6$) δ: 165.6, 165.5, 164.7, 164.6, 138.0, 133.5, 133.4, 133.3, 131.1, 129.6, 129.4, 129.3, 129.2, 129.1, 128.9, 128.8, 128.7, 128.6, 128.5, 128.1, 128.0, 127.8, 127.7, 127.6, 127.4, 127.3, 103.6, 99.9, 99.4, 95.9, 77.2, 74.8, 74.1, 74.0, 73.9, 73.8, 73.5, 72.4, 72.3, 72.0, 71.1, 70.0, 69.9, 69.7, 69.6, 68.9, 68.8, 63.9, 63.8, 63.7, 56.1, 54.4, 28.9, 15.5.

h) O-(2-O-benzyl-3,4-di-O-(4-chlorobenzoyl)-α-L-fucopyranosyl)-(1→2)-O-(6-O-pivaloyl-β-D-galactopyranosyl)-(1→4)-D-glucose From Example 20i, Method A, Colourless Crystal, m.p.: 126-128° C. (Toluene-Acetone).
$^1$H NMR (MeOD, 300 MHz): δ=7.85-7.18 (m, 13H), 5.90-3.45 (m, 21H), 1.22-1.15 (m, 12H).
$^{13}$C NMR (MeOD, 75 MHz): δ=178.7, 165.4, 165.0, 139.8, 139.8, 137.7, 131.1-131.0, 129.0-127.9, 101.0, 96.9, 92.6, 75.1-74.9, 73.1, 72.7, 71.7, 71.5, 70.6, 70.4, 69.7, 64.9, 63.3, 60.2, 38.7, 29.8, 26.5, 15.2.

i) O-(2-O-benzyl-3,4-di-O-benzoyl-α-L-fucopyranosyl)-(1→2)-O-(6-O-pivaloyl-β-D-galactopyranosyl)-(1→4)-D-glucose From Example 20c, Method A
$^1$H NMR (CDCl$_3$): δ=1.2 (m, 12H); 3.00 (m, 1H); 3.10-4.05 (m, 13H); 4.07-4.77 (m, 10H); 5.4-5.8 (m, 4H); 7.15-7.35 (m, 9H); 7.35-7.7 (m, 5H); 7.8 (d, 2H, J=7.9 Hz); 7.9 (d, 2H, J=8.0 Hz).
$^{13}$C NMR (CDCl$_3$): δ=16.27, 27.37, 61.63, 65.41, 65.79, 66.02, 70.82, 70.99, 72.61, 73.23, 73.89, 74.43, 74.57, 75.88, 75.92, 75.96, 76.03, 76.21, 76.24, 76.77, 78.89, 92.38, 96.70, 98.67, 101.56, 128.97, 129.30, 129.39, 129.46, 129.75, 129.82, 130.09, 133.44, 133.49, 133.54, 136.79, 136.95, 166.05, 166.12, 166.17, 166.21, 178.84.

Example 22

O-(2-O-benzyl-α-L-fucopyranosyl)-(1→2)-O-(3,4-isopropylidene-β-D-galactopyranosyl)-(1-4)-2,3:5,6-di-O-isopropylidene-D-glucose dimethyl acetal Compound of example 20a (1.22 g) is dissolved in a solution prepared form 13 mg of NaOH in 5 ml of MeOH and stirred overnight at rt. NaOH is quenched with dry ice and the solvent is evaporated off. The residue is dissolved in TBME (10 ml) and washed with water (3×4 ml). The solvent is evaporated in vacuo and iPr$_2$O (6 ml) is added to obtain a clear solution from which the product precipitates after seeding. The white crystals are filtered, washed and dried (0.49 g). The mother liquor is concentrated and redissolved in MeOH, this solution is washed 3 times with hexane and evaporated. The residue is then redissolved in iPr$_2$O and the solution is seeded, the product is filtered, washed and dried (0.16 g). Overall yield is 0.65 g (83%) of pure triol. M.p.: 146.8-149° C.
$^1$H NMR (CDCl$_3$) δ: 1.23 (d, 3H, J=6.7 Hz); 1.28-1.50 (6s, 18H); 3.49 (s, 3H); 3.51 (s, 3H); 3.6-3.75 (m, 4H); 3.8 (m, 2H); 3.9-4.0 (m, 5H); 4.0-4.15 (m, 4H); 4.27 (q, 1H, J=5.4 Hz); 4.36 (d, 1H, 7 Hz); 4.51-4.57 (m, 2H); 4.63 (dd, 1H, J=7.2 Hz, J=8 Hz); 4.78 (d, 1H, J=11.6 Hz); 5.61 (d, 1H, J=3.67 Hz); 7.25-7.4 (m, 5H).
$^{13}$C NMR (CDCl$_3$) δ: 16.57, 25.20, 26.69, 26.84, 27.32, 28.13, 54.42, 57.95, 62.58, 65.17, 65.73, 69.36, 71.91, 71.98, 74.13, 74.66, 75.14, 75.53, 77.40, 77.82, 78.10, 80.85, 94.30, 101.63, 107.81, 108.97, 109.92, 110.71, 127.85, 127.98, 128.54, 138.55.

Example 23

O-(2-O-(4-methylbenzyl)-α-L-fucopyranosyl)-(1→2)-O-(3,4-isopropylidene-β-D-galactopyranosyl)-(1-4)-2,3:5,6-di-O-isopropylidene-D-glucose dimethyl acetal 0.5M NaOMe in MeOH (5 ml) is added to a solution of compound of example 20d (2.51 g, 2.4 mmol) in methanol (10 ml). The reaction mixture is stirred for 6 h. After completion of the reaction dry ice is added and the solution is concentrated. Chromatography of the residue gives the desired compound (1.15 g, 63%) as a white foam.
The same procedure is applied starting from compound of example 20e (59%), from compound of example 20f (71%) and from compound of example 20g (51%).
$^1$H NMR (CDCl$_3$, 300 MHz): δ=7.20 (d, 2H, J=7.9 Hz), 7.08 (d, 2H, 7.9 Hz), 5.54 (d, 1H, J=3.5 Hz), 4.67 (d, 1H, J=11.5 Hz), 4.59 (t, 1H, J=7.6 Hz), 4.51-4.60 (m, 2H), 4.32 (d, 1H, J=6.9 Hz), 4.26-4.20 (m, 1H), 4.10-3.58 (m, 15H), 3.46 (s, 6H), 2.29 (s, 3H), 1.44-1.17 (m, 21H).
$^{13}$C NMR (CDCl$_3$, 75 MHz): δ=137.6, 135.4, 129.3, 128.2, 110.7, 109.9, 109.0, 107.9, 101.6, 94.3, 80.9, 78.1, 76.1, 75.6, 75.1, 74.7, 74.7, 74.1, 71.9, 71.8, 69.3, 65.7, 65.2, 62.6, 60.6, 58.0, 54.4, 28.1, 27.3, 26.9, 26.8, 26.7, 25.2, 21.4, 16.6, 14.4.

Example 24

O-(2-O-(4-methylbenzyl)-α-L-fucopyranosyl)-(1→2)-O-(β-D-galactopyranosyl)-(1→4)-D-glucose p-Toluenesulfonic acid monohydrate (76 mg, 0.4 mmol, 0.15 eq) is added to a mixture of compound of example 23 (2.0 g, 2.64 mmol) in iPrOH/H$_2$O (2 ml:6 ml). The reaction mixture is stirred at 55° C. and 250 mbar. After 4 hours the pressure is reduced to 90 mbar and the reaction mixture is stirred for another 15 min to remove all organic solvents. The remaining aqueous solution is neutralized with Amberlite IR400 (OH$^-$), the resin is filtrated off and the filtrate is washed with EtOAc (20 ml). The phases are separated and the water phase is freeze dried to give the desired compound (1.53 g, 98%) as a colourless solid.
$^1$H NMR (MeOD, 300 MHz): δ=7.35 (d, 2H, J=7.9 Hz), 7.14 (d, 2H, J=7.9 Hz), 5.50 (m, 1H), 5.14-3.22 (m, 20H), 2.30 (s, 3H), 1.19-1.14 (m, 3H).
$^{13}$C NMR (MeOD, 75 MHz): δ=138.4, 136.3, 129.9, 129.6, 102.2, 98.5, 76.8, 72.9, 69.7, 67.4, 31.7, 21.3, 16.4.

Example 25

O-(2-O-benzyl-α-L-fucopyranosyl)-(1→2)-O-(β-D-galactopyranosyl)-(1→4)-D-glucose a) Compound of example 22 (5.0 g, 6.71 mmol) and H$_2$O/iPrOH (5:2, 20 ml) are added in a flask to give a white suspension. p-TsOH.H$_2$O (0.191 g) is added and the mixture is heated to 55° C. (water temp.) at 250 mbar pressure under stirring. After 4 hours the pressure is decreased to 90 mbar (55° C.) and the clear solution is further stirred under reduced pressure for additional 20 min to remove all organic solvent. The reaction mixture is washed with EtOAc (2×15 ml) and the aqueous phase is neutralized with Amberlite IR400 (OH) resin on column (charged with 5.0 gram of resin). The column is rinsed with water (8 mL) and the aqueous phase is evaporated (50 mbar/45° C.). The crude trisaccharide is dissolved in 2-propanol (25 ml) and heated to 70° C. (oil temp.). The clear solution is slowly cooled to 4° C. over 7 hours and stirred overnight. The obtained solid is filtered off and wash with cold EtOAc and pentane to yield 3.41 g (5.90 mmol, 88%) of white crystals.
Purity of product (HPLC UV): 96.4%. Mp: 153-156° C.
b) Compound of example 21g (400 mg) is dissolved in MeOH (2 ml) and catalytic amount of NaOMe is added to the solution which is stirred at room temperature for 12 hours. Ion exchange resin (H$^+$) is added, the mixture is stirred for 3 minutes to reach pH=7. the resin is filtrated off and the filtrate is evaporated to give a solid product (229 mg, 87%).

c) Methanol (3 ml) is added to the compound of example 21e (1.0 g), then solid NaOMe (10 mg) is added. The mixture is stirred at 40° C. for 10 hours. The reaction mixture is neutralized with HCl/MeOH. Activated charcoal (50 mg) is added and the suspension is stirred for 30 minutes. The charcoal is filtered off, washed with a small portion of MeOH then the clear filtrate is diluted with i-BuOH (3 ml). MeOH is distilled off and a solid, which is precipitated from the solvent, is filtered off, washed with i-BuOH (1.5 ml) and dried to give 510 mg (88%) of white solid.

d) Trisaccharide of example 21f is dissolved in a solution of NaOH in methanol and stirred overnight at rt. The NaOH is quenched with dry ice and the solvent is evaporated off giving the title product in quantitative yield.

e) Recrystallization protocol: the obtained trisaccharide (3.0 g) is dissolved in 2-propanol (22 ml) at 70° C. (oil temp.) and allowed to cool slowly to RT and stirred overnight. White crystals are filtered and washed with cold EtOAc and pentane. Purity of product (HPLC UV): 97.2%. Mp: 155-159° C.

$^1$H NMR (300 MHz, D$_2$O): δ 1.17 (d, 3H, J=6.6 Hz), 3.25 (dd, 0.6H, J=8.1, 9.3 Hz), 3.35-3.91 (m, 14.4H), 4.21 (dq, 1H, J=3.9, 6.6 Hz), 4.49 (d, 1H, J=7.5 Hz), 4.58 (d, 0.6H, J=8.1 Hz), 4.63 (d, 1H, J=11.4 Hz), 4.82 (d, 1H, J=11.4 Hz), 5.17 (d, 0.4H, J=3.6 Hz), 5.46 (d, 1H, J=3.6 Hz), 7.36-7.46 (m, 5H).

$^{13}$C NMR (75 MHz, D$_2$O (using acetone as external reference δ 30.9)): δ 15.9, 60.7, 60.8, 61.8, 67.2, 67.3, 69.4, 69.8, 71.0, 71.9, 72.0, 72.3, 72.6, 74.5, 74.6, 75.0, 75.6, 75.7, 75.9, 75.9, 76.4, 76.5, 92.4, 96.5, 97.5, 100.7, 100.8, 129.0, 129.3, 129.4, 137.8.

Example 26

2'-O-fucosyllactose a) To a solution of compound of example of 25 (5.0 g) in methanol (50 ml) 100 mg 10% palladium on charcoal is added. The suspension is stirred under hydrogen atmosphere at rt for 8 hours. The catalyst is filtered off, washed with water and the filtrate is evaporated to yield the product as amorphous white solid: 4.1 g.

HPLC-MS: ESI+511.2 [M+Na]$^+$, 527.2 [M+K]$^+$; ESI-487.4 [M-H]$^-$, 523.2 [M+Cl]$^-$, 577.3 [M$_2$+H]$^-$.

$^1$H-NMR (600 MHz, D$_2$O) δ: α-D-glucose H-1 5.22 d, H-2 3.59 dd, H-3*3.80 dd, H-4 3.71 dd, H-5 3.91 m, H-6×3.90 m, H-6y 3.80 m; β-D-glucose H-1 4.63 d, H-2 3.29 dd, H-3 3.58 dd, H-4 3.72 dd, H-5 3.47 ddd, H-6×3.94 dd, H-6y 3.76 dd; D-galactose H-1 4.52 d, H-2 3.66 dd, H-3 3.88 m, H-4 3.90 m, H-5 3.81 m, H-6×3.81 m, H-6y 3.74 m; L-fucose H-1 5.30 d, H-2*3.80 m, H-3*3.80 m, H-4 3.82 d, H-5 4.22, 4.25 qd, CH$_3$ 1.22 d.

$^{13}$C-NMR (150 MHz, D$_2$O) δ: α-D-glucose C-1 94.5, C-2 74.0, C-3*72.3, C-4 77.9, C-5 73.1, C-6 62.7; β-D-glucose C-1 98.6, C-2 76.6, C-3 77.0, C-4 78.5, C-5 78.0, C-6 62.9; D-galactose C-1 102.9, C-2 79.0, C-3 76.3, C-4 71.9, C-5 74.0, C-6 63.8; L-fucose C-1 102.0, C-2*72.4, C-3*70.9, C-4 74.4, C-5 69.6, CH$_3$ 18.0. (*interchangeable assignments)

b) To a solution of compound of example of 25 (2.0 g) in methanol (7 ml) and water (1 ml) 200 mg 10% palladium on charcoal is added. The suspension is stirred under hydrogen atmosphere (5 atm) at 50° C. for 0.5 hours. The catalyst is filtered off on a preheated filter, washed with hot water and the filtrate is evaporated to yield 1.6 g of product as white amorphous solid.

LIST OF REFERENCES

1. S. A. Abbas, J. J. Barlow, K. L. Matta, *Carbohydr. Res.* 1981, 88, 51-60.
2. A. Fernandez-Mayoralas, M. Martin-Lomas, *Carbohydr. Res.* 1986, 154, 93-101.
3. R. K. Jain, R. D. Locke, K. L. Matta, *Carbohydr. Res.* 1991, 212, c1-c3.
4. K. L. Matta, R. K. Jain, R. D. Locke, U.S. Pat. No. 5,438, 124A 19950801.
5. M. Izumi, O. Tsuruta, S. Harayama, H. Hashimoto, *J. Org. Chem.* 1997, 62, 992-998.
6. A. Rencurosi, L. Poletti, L. Panza, L. Lay, *J. Carbohydr. Chem.* 2001, 20, 761-765.

ABBREVIATIONS LIST

Ac acetyl
Bn benzyl
BOP-Clbis-(2-oxo-3-oxazolidinyl)-phosphonic chloride
Bz benzoyl
CAN ceric ammonium nitrate
DCC N,N'-dicyclohexylcarbodiimide
DCM dichloromethane
DMF dimethylformamide
DMSO dimethylsulphoxide
ESI electrospray ionization
EtOAc ethyl acetate
2'-FL 2'-O-fucosyllactose
IDCP iodinium di(sym-collidine) perchlorate
Me methyl
MeCN acetonitrile
MTBE methyl t-butyl ether
Ph phenyl
Piv pivaloyl
rt room temperature
TBAB tetrabutylammonium bromide
TBAHStetrabutylammonium hydrogensulphate
TEBAC benzyl triethylammonium chloride
THF tetrahydrofuran
TLC thin layer chromatography
Tr trityl

The invention claimed is:

1. A method for the preparation of 2'-O-fucosyllactose, characterized in that a compound of general formula 1

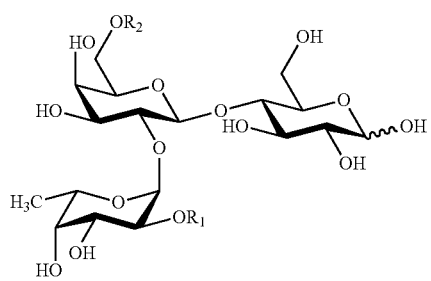

wherein R$_1$ is a group removable by hydrogenolysis and R$_2$ is a group removable by hydrogenolysis or H— or a hydrate or solvate thereof is subjected to catalytic hydrogenolysis.

2. The method according to claim 1, characterized in that the catalytic hydrogenolysis is carried out in water, in one or more C$_1$-C$_6$ alcohols or in a mixture of water and one or more $C_1$-$C_6$ alcohols, in the presence of palladium on charcoal, palladium black or Raney nickel.

3. The method according to claim 1, characterized in that a compound of general formula 1, wherein $R_1$ is benzyl, 4-methylbenzyl, naphthylmethyl, benzyloxycarbonyl, 4-phenylbenzyl, 4-chlorobenzyl, 4-methoxybenzyl, 3,4-dimethoxybenzyl, 2,4,6-trimethylbenzyl or 2,3,4,5,6-pentamethylbenzyl and $R_2$ is H, is applied.

4. A compound selected from the group consisting of:
i) compounds of general formula 1

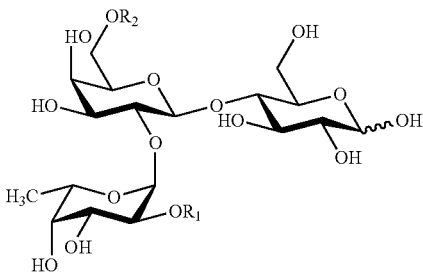

1 wherein $R_1$ is a group removable by hydrogenolysis, $R_2$ is a group removable by hydrogenolysis or H;
ii) compounds of general formula 3

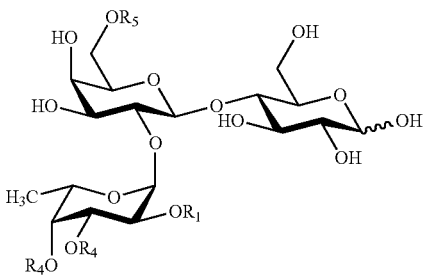

3 wherein $R_1$ is a group removable by hydrogenolysis, $R_4$ is optionally substituted acyl, $R_5$ is a group removable by hydrogenolysis or optionally substituted acyl—or a hydrate or solvate thereof.

5. A method for the preparation of a compound according to claim 4 selected from:
i) a method for the preparation of compounds of general formula 1 defined in claim 4,
characterized in that a compound of general formula 2

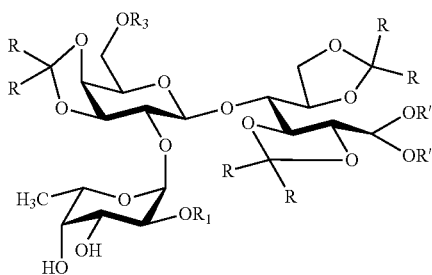

2 wherein $R_1$ is a group removable by hydrogenolysis, $R_3$ is a group removable by hydrogenolysis, acetal type group, silyl group or H, R is alkyl or two geminal R-groups with the carbon atom to which they are attached form a $C_3$-$C_6$ cycloalkyl ring, R' is alkyl—or hydrate or solvate thereof is subjected to acid catalyzed mild hydrolysis;
ii) a method for the preparation of compounds of general formula 1 defined in claim 4, characterized in that a compound of general formula 3

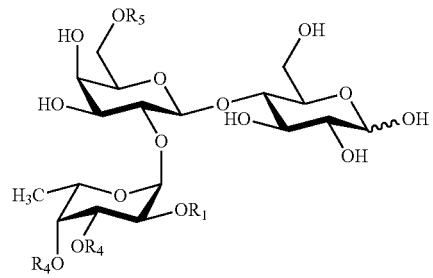

3 wherein $R_1$ is a group removable by hydrogenolysis, $R_4$ is optionally substituted acyl, $R_5$ is a group removable by hydrogenolysis or optionally substituted acyl—or a hydrate or solvate thereof is subjected to deacylation;
iii) a method for the synthesis of a compound of general formula 3 according to claim 4, characterized in that a compound of general formula 4

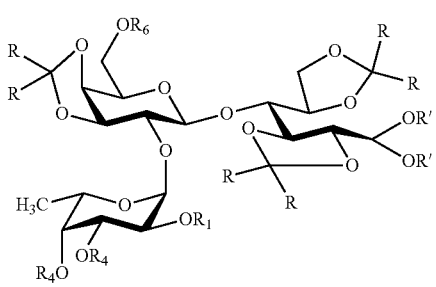

4 wherein $R_1$ is a group removable by hydrogenolysis, $R_4$ is optionally substituted acyl, $R_6$ is a group removable by hydrogenolysis, acetal type group, silyl group or optionally substituted acyl, R is alkyl or two geminal R-groups with the carbon atom to which they are attached form a $C_3$-$C_6$ cycloalkyl, R' is alkyl—or a hydrate or solvate thereof.

6. The compound of formula 1 according to claim 4, wherein $R_1$ is benzyl, 4-methylbenzyl, naphthylmethyl, benzyloxycarbonyl, 4-phenylbenzyl, 4-chlorobenzyl, 4-methoxybenzyl, 3,4-dimethoxybenzyl, 2,4,6-trimethylbenzyl or 2,3,4,5,6-pentamethylbenzyl, and $R_2$ is H.

7. The compound of formula 3 according to claim 4, wherein $R_1$ is benzyl, 4-methylbenzyl, naphthylmethyl, benzyloxycarbonyl, 4-phenylbenzyl, 4-chlorobenzyl, 4-methoxybenzyl, 3,4-dimethoxybenzyl, 2,4,6-trimethylbenzyl or 2,3,4,5,6-pentamethylbenzyl, $R_4$ is benzoyl or 4-chlorobenzoyl and $R_5$ is pivaloyl, benzoyl or 4-chlorobenzoyl.

8. The method for the preparation of a compound of formula 1 from a compound of formula 2 according to claim 5, characterized in that acid catalyzed mild hydrolysis is carried out in a mixture of water and one or more $C_1$-$C_6$ alcohols in the presence of a sulfonic acid.

9. The method for the preparation of a compound of formula 1 from a compound of formula 2 according to claim 5, characterized in that a compound of general formula 2, wherein $R_1$ is benzyl, 4-methylbenzyl, naphthylmethyl, benzyloxycarbonyl, 4-phenylbenzyl, 4-chlorobenzyl, 4-methoxybenzyl, 3,4-dimethoxybenzyl, 2,4,6-trimethylbenzyl or 2,3,4,5,6-pentamethylbenzyl, $R_3$ is H, and R and R' are methyl, is applied.

10. The method for the preparation of a compound of formula 1 from a compound of formula 3 according to claim 5, characterized in that deacylation is carried out in methanol in the presence of NaOMe or NaOH.

11. The method for the preparation of a compound of formula 1 from a compound of formula 3 according to claim 5, characterized in that a compound of general formula 3, wherein $R_1$ is benzyl, 4-methylbenzyl, naphthylmethyl, benzyloxycarbonyl, 4-phenylbenzyl, 4-chlorobenzyl, 4-methoxybenzyl, 3,4-dimethoxybenzyl, 2,4,6-trimethylbenzyl or 2,3,4,5,6-pentamethylbenzyl, $R_4$ is benzoyl or 4-chlorobenzoyl and $R_5$ is pivaloyl, benzoyl or 4-chlorobenzoyl, is applied.

12. The method for the preparation of a compound of formula 3 from a compound of formula 4 according to claim 5, characterized in that acid catalyzed mild hydrolysis is carried out in aqueous acetonitrile or in aqueous acetone in the presence of p-toluenesulphonic acid or HCl.

13. The method for the preparation of a compound of formula 3 from a compound of formula 4 according to claim 5, characterized in that a compound of general formula 4, wherein $R_1$ is benzyl, 4-methylbenzyl, naphthylmethyl, benzyloxycarbonyl, 4-phenylbenzyl, 4-chlorobenzyl, 4-methoxybenzyl, 3,4-dimethoxybenzyl, 2,4,6-trimethylbenzyl or 2,3,4,5,6-pentamethylbenzyl, $R_4$ is benzoyl or 4-chlorobenzoyl, $R_6$ is pivaloyl, benzoyl or 4-chlorobenzoyl, and R and R' is methyl, is applied.

14. The method according to claim 1, wherein a compound of general formula 1 is prepared from a compound of general formula 2, characterized in that a compound of general formula 2

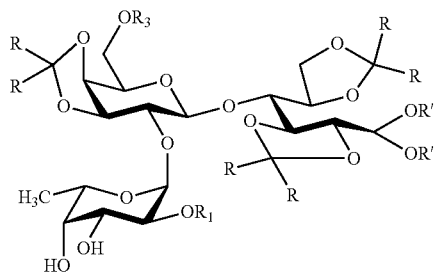

wherein $R_1$ is a group removable by hydrogenolysis, $R_3$ is a group removable by hydrogenolysis, acetal type group, silyl group or H, R is alkyl or two geminal R-groups with the carbon atom to which they are attached form a $C_3$-$C_6$ cycloalkyl ring, R' is alkyl—or hydrate or solvate thereof is subjected to acid catalyzed mild hydrolysis.

15. The method according to claim 1, wherein a compound of general formula 1 is prepared from a compound of general formula 3, characterized in that a compound of general formula 3

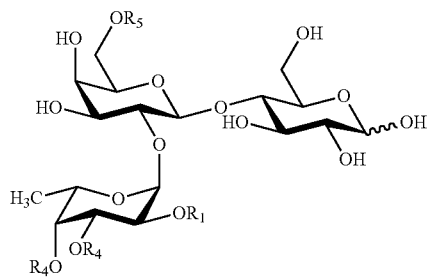

wherein $R_1$ is a group removable by hydrogenolysis, $R_4$ is optionally substituted acyl, $R_5$ is a group removable by hydrogenolysis or optionally substituted acyl—or a hydrate or solvate thereof is subjected to deacylation.

16. The method according to claim 14, wherein a compound of general formula 2 is prepared from a compound of general formula 4, characterized in that a compound of general formula 4

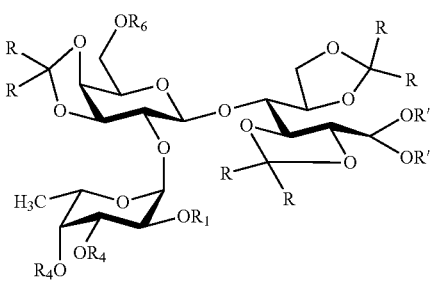

wherein $R_1$ is a group removable by hydrogenolysis, $R_4$ is optionally substituted acyl, $R_6$ is a group removable by hydrogenolysis, acetal type group, silyl group or optionally substituted acyl, R is alkyl or two geminal R-groups with the carbon atom to which they are attached form a $C_3$-$C_6$ cycloalkyl, R' is alkyl—or a hydrate or solvate thereof is deacylated.

17. The method according to claim 15, wherein a compound of general formula 3 is prepared from a compound of general formula 4, characterized in that a compound of general formula 4

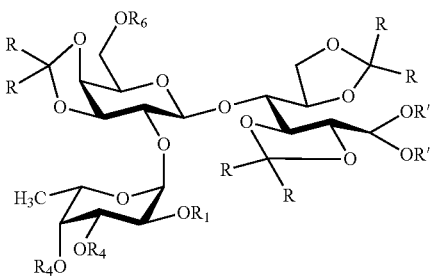

wherein $R_1$ is a group removable by hydrogenolysis, $R_4$ is optionally substituted acyl, $R_6$ is a group removable by hydrogenolysis, acetal type group, silyl group or optionally substituted acyl, R is alkyl or two geminal R-groups with the carbon atom to which they are attached form a $C_3$-$C_6$ cycloalkyl, R' is alkyl—or a hydrate or solvate thereof is subjected to acid catalyzed mild hydrolysis.

18. The method according to claim 16, wherein a compound of general formula 4 is prepared from a compound of general formula 5 and a compound of general formula 6, characterized in that a compound of general formula 5

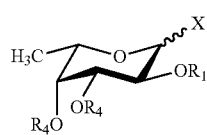

5 wherein $R_1$ is a group removable by hydrogenolysis, $R_4$ is optionally substituted acyl, and X is halogen, —OC(=NH)CCl$_3$, —O-pentenyl, —OAc, —OBz or —SR$_7$, in which $R_7$ is alkyl or optionally substituted phenyl—is reacted with a compound of general formula

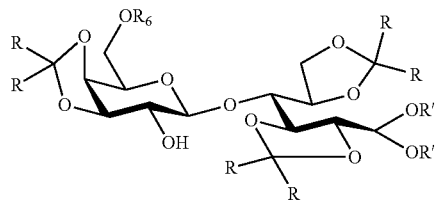

6 wherein $R_6$ is a group removable by hydrogenolysis, acetal type group, silyl group or optionally substituted acyl, R is alkyl or two geminal R-groups with the carbon atom to which they are attached form a $C_3$-$C_6$ cycloalkyl, and R' is alkyl—under glycosylation condition.

19. The method according to claim 17, wherein a compound of general formula 4 is prepared from a compound of general formula 5 and a compound of general formula 6, characterized in that a compound of general formula 5

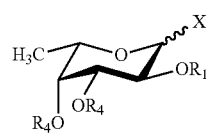

5 wherein $R_1$ is a group removable by hydrogenolysis, $R_4$ is optionally substituted acyl, and X is halogen, —OC(=NH)CCl$_3$, —O-pentenyl, —OAc, —OBz or —SR$_7$, in which $R_7$ is alkyl or optionally substituted phenyl—is reacted with a compound of general formula

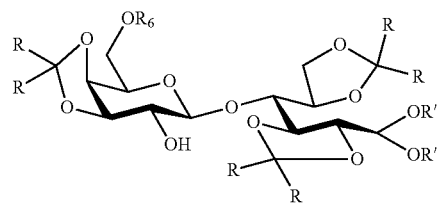

6 wherein $R_6$ is a group removable by hydrogenolysis, acetal type group, silyl group or optionally substituted acyl, R is alkyl or two geminal R-groups with the carbon atom to which they are attached form a $C_3$-$C_6$ cycloalkyl, and R' is alkyl—under glycosylation condition.

\* \* \* \* \*